(12) United States Patent
Buster et al.

(10) Patent No.: US 9,408,634 B2
(45) Date of Patent: Aug. 9, 2016

(54) UTERINE LAVAGE FOR EMBRYO RETRIEVAL

(71) Applicant: Previvo Genetics, LLC, Piedmont, CA (US)

(72) Inventors: John E. Buster, Providence, RI (US); Moses Cesario, Piedmont, CA (US); Steven Paul Woodard, Cupertino, CA (US)

(73) Assignee: Previvo Genetics, Inc., San Jose, CA (US)

(*) Notice: Subject to any disclaimer, the term of this patent is extended or adjusted under 35 U.S.C. 154(b) by 0 days.

(21) Appl. No.: 14/132,235

(22) Filed: Dec. 18, 2013

(65) Prior Publication Data

US 2014/0378756 A1    Dec. 25, 2014

Related U.S. Application Data

(63) Continuation of application No. 13/924,520, filed on Jun. 21, 2013.

(51) Int. Cl.
*A61B 17/435* (2006.01)
*A61B 17/42* (2006.01)
*A61B 19/02* (2006.01)

(52) U.S. Cl.
CPC .............. *A61B 17/435* (2013.01); *A61B 17/42* (2013.01); *A61B 2017/4216* (2013.01);
(Continued)

(58) Field of Classification Search
CPC ................ A61B 17/435; A61B 17/42; A61B 2017/4216; A61B 2217/4216; A61B 2217/005; A61B 2019/0254; A61B 2019/0265; A61B 2019/025

USPC ........... 600/573–580, 33–36; 604/27, 35, 36, 604/39–43, 93.01
See application file for complete search history.

(56) References Cited

U.S. PATENT DOCUMENTS 3,587,588 A * 6/1971 Murr ............................ 606/191
4,100,923 A    7/1978 Southern
(Continued)

FOREIGN PATENT DOCUMENTS

EP        131166 B1     9/1988
EP      1870451 A1    12/2007
(Continued)

OTHER PUBLICATIONS

International Search Report and Written Opinion for International Application No. PCT/US12/66828, mailed Apr. 17, 2013.
(Continued)

*Primary Examiner* — Samuel Gilbert
(74) *Attorney, Agent, or Firm* — Fish & Richardson P.C.

(57) ABSTRACT

A device for recovering one or more blastocysts from the uterus of a human includes an outer guide member for insertion into a cervical canal of the human. The outer guide member includes a distal portion with an activatable seal for isolating the uterus from the external environment and defines a lumen having a longitudinal axis. The device also includes an inner catheter located within the lumen and slidable along the longitudinal axis of the lumen relative to the outer guide member. The inner catheter has a distal tip positionable distally of the seal to extend into the uterus and includes a fluid delivery lumen terminating at a distal fluid delivery port for delivering fluid into the uterus. The device defines a distal suction port for aspirating fluid and entrained blastocysts from the uterus. The distal fluid delivery port and the distal suction port are arranged such that, in use, fluid delivered from the distal fluid delivery port travels through the distal suction port to the uterus.

15 Claims, 54 Drawing Sheets

(52) U.S. Cl.
CPC .. *A61B 2019/025* (2013.01); *A61B 2019/0254* (2013.01); *A61B 2019/0265* (2013.01); *A61B 2050/185* (2016.02); *A61B 2050/311* (2016.02); *A61B 2217/005* (2013.01); *A61B 2217/007* (2013.01)

(56) References Cited

U.S. PATENT DOCUMENTS

| | | | |
|---|---|---|---|
| 4,178,936 A | 12/1979 | Newcomb | |
| 4,468,216 A * | 8/1984 | Muto | 604/43 |
| 4,533,345 A | 8/1985 | Louw | |
| 4,601,698 A | 7/1986 | Moulding | |
| 5,005,583 A | 4/1991 | Bustillo | |
| 5,030,202 A | 7/1991 | Harris | |
| 5,217,466 A | 6/1993 | Hasson | |
| 5,409,457 A * | 4/1995 | del Cerro et al. | 604/521 |
| 5,421,346 A * | 6/1995 | Sanyal | 600/563 |
| 5,445,168 A | 8/1995 | Krebs | |
| 5,514,119 A | 5/1996 | Curtis | |
| 5,938,098 A | 8/1999 | Fife | |
| 6,106,506 A | 8/2000 | Abell et al. | |
| 6,234,958 B1 * | 5/2001 | Snoke et al. | 600/114 |
| 6,287,863 B1 | 9/2001 | Hodgson | |
| 6,436,072 B1 | 8/2002 | Kullas et al. | |
| 6,485,452 B1 * | 11/2002 | French et al. | 604/39 |
| 6,827,703 B1 | 12/2004 | Ackerman | |
| 6,939,336 B2 * | 9/2005 | Silfver | 604/515 |
| 7,378,338 B2 | 5/2008 | Cabral | |
| 7,378,388 B2 | 5/2008 | Seifer et al. | |
| 7,419,500 B2 | 9/2008 | Marko | |
| 7,963,946 B2 * | 6/2011 | Moubayed et al. | 604/151 |
| 8,052,669 B2 | 11/2011 | Lee-Sepsick et al. | |
| 8,221,403 B2 | 7/2012 | Sharkey et al. | |
| 8,257,244 B2 | 9/2012 | Mock | |
| 8,316,853 B2 | 11/2012 | Lee-Sepsick | |
| 8,316,854 B2 | 11/2012 | Lee-Sepsick | |
| 8,336,552 B2 | 12/2012 | Lee-Sepsick | |
| 8,585,616 B2 | 11/2013 | Swann | |
| 2002/0115054 A1 | 8/2002 | Forest | |
| 2003/0108586 A1 | 6/2003 | Ramey | |
| 2004/0022739 A1 | 2/2004 | Daniels et al. | |
| 2004/0083498 A1 | 4/2004 | DeSousa | |
| 2004/0219028 A1 | 11/2004 | Demarais et al. | |
| 2004/0267198 A1 * | 12/2004 | Torstensen et al. | 604/104 |
| 2005/0049199 A1 | 3/2005 | Hillier et al. | |
| 2005/0235374 A1 | 10/2005 | Bunschoten et al. | |
| 2005/0256464 A1 * | 11/2005 | Pallas | 604/319 |
| 2006/0069031 A1 | 3/2006 | Loumaye | |
| 2006/0135405 A1 | 6/2006 | Rischer et al. | |
| 2006/0217315 A1 | 9/2006 | Bennink et al. | |
| 2006/0247177 A1 | 11/2006 | Millar | |
| 2007/0135706 A1 | 6/2007 | Shimko et al. | |
| 2007/0213671 A1 * | 9/2007 | Hiatt | A61M 25/007 604/164.01 |
| 2008/0071210 A1 | 3/2008 | Moubayed et al. | |
| 2008/0091119 A1 | 4/2008 | Moffitt | |
| 2008/0103446 A1 | 5/2008 | Torrance et al. | |
| 2008/0172013 A1 | 7/2008 | Kucklick | |
| 2008/0245371 A1 | 10/2008 | Gruber | |
| 2009/0024108 A1 | 1/2009 | Lee-Sepsick | |
| 2009/0054871 A1 | 2/2009 | Sharkey | |
| 2010/0086492 A1 | 4/2010 | Lee-Sepsick | |
| 2010/0106108 A1 | 4/2010 | Hirsch | |
| 2010/0160717 A1 | 6/2010 | Scott, Jr. et al. | |
| 2010/0303688 A1 | 12/2010 | Andersen | |
| 2011/0002273 A1 | 1/2011 | Youn | |
| 2011/0022073 A1 | 1/2011 | Gross et al. | |
| 2011/0098524 A1 | 4/2011 | Barcelo | |
| 2011/0105834 A1 | 5/2011 | Wong | |
| 2012/0197245 A1 | 8/2012 | Burnett et al. | |
| 2013/0150418 A1 | 6/2013 | Goedeke et al. | |
| 2013/0165744 A1 | 6/2013 | Carson et al. | |
| 2014/0031631 A1 | 1/2014 | Hall et al. | |

FOREIGN PATENT DOCUMENTS

| | | |
|---|---|---|
| EP | 1987814 A1 | 5/2008 |
| EP | 1987820 A1 | 11/2008 |
| JP | 2007045790 A | 2/2007 |
| WO | WO8200754 A1 | 3/1982 |
| WO | WO8807056 A1 | 9/1988 |
| WO | WO9943365 A1 | 9/1999 |
| WO | 2010118325 | 10/2010 |
| WO | WO2011032984 A1 | 3/2011 |
| WO | 2014140217 | 12/2014 |

OTHER PUBLICATIONS

Formigli, L., et al., "Non-Surgical Flushing of the Uterus for Pre-Embryo Recovery: Possible Clinical Applications", Centre for Reproductive Medicine and CECOS-Milan, Viale Umbria, 44, 20135 Milano, Italy, Human Reproduction vol. 5, No. 3, pp. 329-335, 1990 (7 pages).

Buster, J., et al, "First Birth: Letters," Jama, The Journal of the American Medical Association, Feb. 17, 1984 (1 page).

Buster, John E. and Sandra A. Carson, "Genetic Diagnosis of the Preimplantation Embryo", American Journal of Medical Genetics 34:211-216 (1989) (6 pages).

Buster, John E., "The First Live", SRM vol. 6 No. 4, Nov. 2008, pp. 22-28 (7 pages).

Sauer, Mark V., et al., "An Instrument for the Recovery of Preimplantation Uterine Ova", Obstetrics & Gynecology, 0029-7844/88, vol. 71, No. 5, May 1988, pp. 804-806 (3 pages).

Seidel, George E. Jr., "Superovulation and Embryo Transfer in Cattle", downloaded from www.sciencemag.org on Nov. 18, 2011, Science, vol. 211, 23, Jan. 1981, pp. 351-358 (8 pages).

Croxotto, HB, et al., "Attempts to Modify Ovum Transport in Women", J. Reprod Fertil. Jan. 1979:55 (1):231-237.

Diaz, S., et al., "Studies on the duration of ovum transport by the human oviduct. III. Time interval between the luteinizing hormone peak and recovery of ova by transcervical flushing of the uterus in normal women." American Journal of Obstetrics and Gynecology, May 1, 1980; 13791):116-21., retrieved from http://www.ncbi.nim. nih.gov/pubmed/7369274 on Nov. 20, 2011 (1 page).

Croxatto, HB, et al., "Studies on the duration of egg transport by the human oviduct. II. Ovum location at various intervals following luteinizing hormone peak", American Journal of Obstetrics and Gynecology, Nov. 15, 1978:132(6);629-34, retrieved from http://www.ncbi.nlm.gov/pubmed/71746 on Nov. 20, 2011 (1 page).

Sauer, Mark V., et al., "Pregnancy following nonsurgical donor transfer to a functionally agonadal woman", Fertility and Sterility, The American Fertility Society, vol. 48, No. 2, Aug. 1987 (2 pages).

Sauer, MV, et al., "In-vivo blastocyst production and ovum yield among fertile women", Human Reproduction, Nov. 1987; 2(8):701-3, PubMed, Department of Obstetrics and Gynecology, Harbor-UCLA Medical Center, Torrance, PMID: 3437049, http://www.ncbi.nlm.nih.gov/pubmed?term=sauer . . . Retrieved from Internet on Oct. 21, 2011 (1 page).

Buster, John E., "Embryo Donation by Uterine Flushing and Embryo Transfer", Clinics in Obstetrics and Gynaecology, vol. 12, No. 4, Dec. 1985, pp. 815-824 (10 pages).

Bustillo, Maria, MD, et al., "Nonsurgical Ovum Transfer as a Treatment in Infertile Women: Preliminary Experience", Jama: The Journal of the American Medical Association, Mar. 2, 1984, vol. 251, No. 9, pp. 1171-1173 (3 pages).

Carson, Sandra, A., "Superovulation Fails to Increase Human Blastocyst Yield After Uterine Lavage", Prenatal Diagnosis, vol. 11, 513-522 (1991) (10 pages).

Buster, J.E., et al. "Non-surgical transfer of in vivo fertilised donated ova to five infertile women: report of two pregnancies", announcing the First Two Ongoing Pregnancies, reprinted from The Lancet, Jul. 23, 1983, p. 223-224.

Buster, J.E. et al. "Non-surgical transfer of an in-vivo fertilised donated ovum to an infertility patient," First Transfer and Failure, The Lancet, Apr. 9, 1983.

Buster, J.E., et al. Clinical Articles: Third Birth, "Biologic and morphologic development of donated human ova recovered by non-

(56) References Cited

OTHER PUBLICATIONS surgical uterine lavage," Torrance, California, reprinted from American Journal of Obstetrics and Gynecology, St. Louis, vol. 153, No. 2, pp. 211-217, Sep. 15, 1985.
Bustillo, M., et al. "Nonsurgical ovum transfer as a treatment for intractable infertility: What effectiveness can we realistically expect?" Jun. 15, 1984, American Journal of Obstetrics and Gynecology, pp. 371-375.
The New York Times, "Screening Embryos for Future Disease," copyright 2006, retrieved from the Internet from website: http://www.nytimes.com/imagespages/2006/09/02/health/20060903_GENE_GRAPHIC.html.
Wade, Nicholas, "Treatment for Blood Disease is Gene Therapy Landmark," The New York Times, Hemophilia B Gene Therapy Breakthrough—NYTimes.com, Dec. 10, 2011.
Office Action for U.S. Appl. No. 13/335,170, mailed Jul. 18, 2014, 33 pages.
Lainas, T.G., et al., "Management of Severe Early Ovarian Hyperstimulation Syndrome by Re-Initiation of GnRH Antagonist," RBM Online, vol. 15, No. 4, 2007, 408-412, Reproductive BioMedicine Online; www.rbmonline.com/Article/2880 on web Aug. 20, 2007.
Lainas, T.G., et al., "Management of Severe OHSS using GnRH Antagonist and Blastocyst Cryopreservation in PCOS Patients Treated with Long Protocol," RBM Online, vol. 18, No. 1, 2009, 15-20, Reproductive BioMedicine Online; www.rbmonline.com/Article/3470 on web Nov. 5, 2008.
Lainas, T.G., et al., "Live Births after Management of Severe OHSS using GnRH Antagonist Administration in the Luteal Phase," RBM Online, vol. 19, No. 6, 2009, 789-795, Reproductive BioMedicine Online; www.rbmonline.com/Article/4166 on web Oct. 3, 2009.
Lainas, T.G., et al., "Outpatient Management of Severe Early OHSS by Administration of GnRH Antagonist in the Luteal Phase: An Observational Cohort Study," Reproductive Biology and Endocrinology, 2012, 10:69; http://www.rbej.com/10/1/69.
Office Action for U.S. Appl. No. 13/924,470, mailed Jan. 14, 2015.
Office Action for U.S. Appl. No. 13/924,520, mailed Feb. 17, 2015.
Office Action for U.S. Appl. No. 14/250,240, mailed Feb. 11, 2015.
Office Action for U.S. Appl. No. 13/335,170, mailed Mar. 10, 2015.
International Search Report and Written Opinion for International Application No. PCT/US14/43664, mailed Mar. 10, 2015.
Office Action for U.S. Appl. No. 13/924,510, mailed Apr. 27, 2015.
Office Action for U.S. Appl. No. 13/924,494, mailed Apr. 28, 2015.
Office Action for U.S. Appl. No. 13/924,520, mailed Jul. 1, 2015.
Partial European Search Report for European Application No. 12860540.9, mailed Jul. 15, 2015.
International Search Report and Written Opinion in International Application No. PCT/US2015/019465, mailed Jun. 4, 2015, 14 pages.
Office Action for U.S. Appl. No. 14/814,151, mailed Sep. 30, 2015.
Office Action for U.S. Appl. No. 14/814,252, mailed Sep. 22, 2015.
Office Action for U.S. Appl. No. 14/814,184, mailed Nov. 23, 2015.
Office Action for U.S. Appl. No. 14/814,151, mailed Dec. 10, 2015.
Extended European Search Report for European Aplication No. 12860540.9, mailed Dec. 22, 2015.
Extended European Search Report for European Application No. 15191684.8, issued Apr. 29, 2016.
"Cetrotide™ (Cetrorelix Acetate for Injection) 0.25 MG and 3 MG for Subcutaneous Use Only," European Journal of Obstetrics & Gynecology and Reproductive Biology, Elsevier Ireland Ltd., Nov. 8, 2000.
Ilan Tur-Kaspa et al., "GnRH Antagonist, Cetrorelix, for Pituitary Suppression in Modern, Patient-Friendly Assisted Reproductive Technology," Expert Opinion on Drug Metabolism & Toxicology, vol. 5, No. 10, Sep. 17, 2009, pp. 1323-1336.
Kulier, R., et al., "Medical Methods for First Trimester Abortion," Cochrane Database Syst Rev., No. 11, Nov. 2011, p. CD002855.

* cited by examiner

UTERINE LAVAGE FOR EMBRYO RETRIEVAL

This application is a continuation of U.S. patent application Ser. No. 13/924,520, filed Jun. 21, 2013, titled "UTERINE LAVAGE FOR EMBRYO RETRIEVAL," whose disclosure is related to U.S. patent application Ser. No. 13/335,170, filed Dec. 22, 2011, titled "RECOVERY AND PROCESSING OF HUMAN EMBRYOS FORMED IN VIVO," U.S. patent application Ser. No. 13/924,470, filed Jun. 21, 2013, titled "UTERINE LAVAGE FOR EMBRYO RETRIEVAL," U.S. patent application Ser. No. 13/924,494, filed Jun. 21, 2013, titled "UTERINE LAVAGE FOR EMBRYO RETRIEVAL," U.S. patent application Ser. No. 13/924,510, filed Jun. 21, 2013, titled "UTERINE LAVAGE FOR EMBRYO RETRIEVAL," and U.S. patent application Ser. No. 13/924,517, filed Jun. 21, 2013, titled "UTERINE EMBRYO RETRIEVAL," hereby incorporated by reference in their entirety.

TECHNICAL FIELD

This disclosure relates to uterine lavage.

BACKGROUND

Uterine lavage for recovery and re-implantation of human embryos from human subjects has been performed for the past three decades. In particular, in-vivo fertilized embryos have been recovered from fertile women and transferred to infertile recipient women, producing donor-to-recipient transplanted human pregnancies. The first reported procedure was performed by a University of Los Angeles team in 1983 and produced a live birth in 1984.

SUMMARY

In general, in an aspect, at a time when a woman's uterus contains in vivo fertilized preimplantation blastocysts, a seal is provided, between the uterus and the external environment, against flow of fluid from the uterus to the external environment. While the seal is provided, fluid is delivered past the seal and into the uterus. The delivered fluid is withdrawn, with the blastocysts, past the seal and from the uterus to the external environment.

Implementations may include one or more of the following features. The recovered in vivo pre-implantation blastocysts are recovered for genetic diagnosis or genetic therapy or sex determination or any combination of two or more of them. One or more of the blastocysts are returned to the uterus of the woman. The one or more blastocysts are returned to the uterus of the woman without having frozen the blastocysts. The blastocysts resulted from artificial insemination. The blastocysts resulted from causing superovulation in the woman. At least one of the pre-implantation blastocysts is treated. The treating includes gene therapy. The in vivo fertilized preimplantation blastocysts are withdrawn from the uterus with an efficiency of greater than 50%. The in vivo fertilized preimplantation blastocysts are withdrawn from the uterus with an efficiency of greater than 80%. The in vivo fertilized preimplantation blastocysts are withdrawn from the uterus with an efficiency of greater than 90%. The in vivo fertilized preimplantation blastocysts are withdrawn from the uterus with an efficiency of greater than 95%. The embryos are frozen. The delivering or withdrawing or both of the fluid is pulsatile. The fluid is withdrawn while the seal is being provided. The seal enables essentially all of the fluid to be withdrawn. The withdrawing of fluid includes aspirating the fluid from the uterus. Both the delivering and the withdrawing are pulsatile and the pulses of the delivering of the fluid and of the withdrawing of the fluid are coordinated.

In a general aspect, a device for recovering one or more blastocysts from the uterus of a human includes an outer guide member for insertion into a cervical canal of the human. The outer guide member includes a distal portion with an activatable seal for isolating the uterus from the external environment, and the outer guide member defines a lumen having a longitudinal axis. The device also includes an inner catheter located within the lumen and slidable along the longitudinal axis of the lumen relative to the outer guide member. The catheter has a distal tip positionable distally of the seal to extend into the uterus. The inner catheter includes a fluid delivery lumen terminating at a distal fluid delivery port for delivering fluid into the uterus. The device defines a distal suction port for aspirating fluid and entrained blastocysts from the uterus. The distal fluid delivery port and the distal suction port are arranged such that in use fluid delivered from the distal fluid delivery port travels through the distal suction port to the uterus.

Implementations may include one or more of the following features. For example, the inner catheter may include a tubular member that surrounds the fluid delivery lumen. The tubular member may define the first distal suction port proximally of the distal fluid delivery port. The inner catheter may include an atraumatic tip positioned distally of the fluid delivery port. The distal fluid delivery port may be non-circular in shape to provide directional control of fluid spray. The activatable seal may be a balloon collar. The activatable seal may be an expandable foam.

In another general aspect, a system for recovering one or more blastocysts from the uterus of a human includes a device and a controller programmed to cyclically deliver lavage liquid to the uterus via the fluid delivery lumen and apply vacuum to the device from a vacuum source remote from the device. The device includes an outer guide member for insertion into a cervical canal of the human. The outer guide member includes a distal portion with an activatable seal for isolating the uterus from the external environment. The outer guide member defines a lumen having a longitudinal axis. The device also includes an inner catheter located within the lumen and slidable along the longitudinal axis of the lumen relative to the outer guide member. The catheter has a distal tip positionable distally of the seal to extend into the uterus. The inner catheter includes a fluid delivery lumen terminating at a distal fluid delivery port for delivering fluid into the uterus. The device defines a distal suction port for aspirating fluid and entrained blastocysts from the uterus. The distal fluid delivery port and the distal suction port are arranged such that in use fluid delivered from the distal fluid delivery port travels through the distal suction port to the uterus.

Implementations may include one or more of the following features. For example, the controller may include a pump for delivering the lavage liquid and a pump for applying the vacuum. The controller may include electro-mechanical means for controlling the delivery of lavage fluid and the application of vacuum. The controller may be programmed to cyclically deliver varying amount of lavage liquid. The system may further include a lavage fluid bag for supplying the lavage liquid. The system may further include an embryo recovery trap for receiving the aspirated fluid and entrained blastocysts.

In another general aspect, a process for recovering one or more blastocysts from the uterus of a human includes placing a device trans-vaginally into the cervical canal. The device includes an outer guide member and an inner catheter located within the outer guide member. The outer guide member includes a seal for isolating the uterus from the external environment. The process also includes advancing the inner catheter relative to the outer guide member positioning a distal region of the inner catheter within the uterus, delivering fluid through the inner catheter to the uterus, and applying a vacuum to the uterus to aspirate fluid and entrained blastocysts from the uterus. A distal fluid delivery port and a distal suction port are arranged such that in use fluid delivered from the distal fluid delivery port travels through the distal suction port to the uterus.

Implementations may include one or more of the following features. For example, placing the device may include locating the seal in the cervical canal. Locating the seal may include locating the seal between the internal cervical os and the external cervical os such that the seal does not extend into the vagina or the uterus.

In another general aspect, a process for recovering one or more blastocysts from the uterus of a human includes placing a device trans-vaginally into the cervical canal and cyclically delivering fluid through the device to the uterus and applying a vacuum to the uterus to aspirate fluid and entrained blastocysts from the uterus without introducing air into the uterus. A distal fluid delivery port and a distal suction port are arranged such that in use fluid delivered from the distal fluid delivery port travels through the distal suction port to the uterus.

Implementations may include one or more of the following features. For example, cyclically delivering fluid may include increasing the amount of fluid delivered between cycles.

In another general aspect, a device for recovering one or more blastocysts from the uterus of a human includes an outer guide member for insertion into a cervical canal of the human. The outer guide member includes a distal portion with an activatable seal for isolating the uterus from the external environment and a cervical stop adjustably mounted on the outer guide member relative to the seal for positioning against the external cervical os. The outer guide member defines a lumen having a longitudinal axis. The device also includes an inner catheter located within the lumen and slidable along the longitudinal axis of the lumen relative to the outer guide member. The catheter has a distal tip positionable distally of the seal to extend into the uterus. The inner catheter includes a fluid delivery lumen terminating at a distal fluid delivery port for delivering fluid into the uterus. The device defines a distal suction port for aspirating fluid and entrained blastocysts from the uterus.

Implementations may include one or more of the following features. For example, the device may include markings for setting a distance between the seal and the cervical stop.

In another general aspect, a device for recovering one or more blastocysts from the uterus of a human includes an outer guide member for insertion into a cervical canal of the human. The outer guide member includes a distal portion with an activatable seal for isolating the uterus from the external environment and a cervical stop for positioning against the external cervical os. The seal has a length in the range of about 3 to 8 mm, and the outer guide member defines a lumen having a longitudinal axis. The device also includes an inner catheter located within the lumen and slidable along the longitudinal axis of the lumen relative to the outer guide member. The catheter has a distal tip positionable distally of the seal to extend into the uterus. The inner catheter includes a fluid delivery lumen terminating at a distal fluid delivery port for delivering fluid into the uterus. The device defines a distal suction port for aspirating fluid and entrained blastocysts from the uterus.

In another general aspect, a device for recovering one or more blastocysts from the uterus of a human includes an outer guide member for insertion into a cervical canal of the human. The outer guide member includes a distal portion with an activatable seal for isolating the uterus from the external environment. The outer guide member defines a lumen having a longitudinal axis. The device also includes an inner catheter located within the lumen and slidable along the longitudinal axis of the lumen relative to the outer guide member. The catheter has a distal tip positionable distally of the seal to extend into the uterus. The inner catheter includes a fluid delivery lumen terminating at a distal fluid delivery port for delivering fluid into the uterus. The device defines a distal suction port for aspirating fluid and entrained blastocysts from the uterus. The device includes indicia located on the device to be external of the human during use, the indicia providing an indication of the position of the device.

In another general aspect, a device for recovering one or more blastocysts from the uterus of a human includes an outer guide member for insertion into a cervical canal of the human. The outer guide member includes a distal portion with an activatable seal for isolating the uterus from the external environment. The outer guide member defines a lumen having a longitudinal axis. The device also includes an inner catheter located within the lumen and slidable along the longitudinal axis of the lumen relative to the outer guide member. The catheter has a distal tip positionable distally of the seal to extend into the uterus. The inner catheter includes a fluid delivery lumen terminating at a distal fluid delivery port for delivering fluid into the uterus. The device defines a distal suction port for aspirating fluid and entrained blastocysts from the uterus. The outer guide member and the inner catheter are integrated in the device such that an operator cannot remove the inner catheter from the outer guide member without damaging the device.

In another general aspect, a device for recovering one or more blastocysts from the uterus of a human includes an outer guide member for insertion into a cervical canal of the human. The outer guide member includes a distal portion with an activatable seal for isolating the uterus from the external environment. The outer guide member defines a lumen having a longitudinal axis. The device also includes an inner catheter located within the lumen and slidable along the longitudinal axis of the lumen relative to the outer guide member. The catheter has a distal tip positionable distally of the seal to extend into the uterus. The inner catheter includes a fluid delivery lumen terminating at a distal fluid delivery port for delivering fluid into the uterus. The device defines a distal suction port for aspirating fluid and entrained blastocysts from the uterus. The outer guide member and the inner catheter are integrated in the device with the inner catheter having a fixed maximum excursion in proximal and distal directions within the outer guide member.

In another general aspect, a device for recovering one or more blastocysts from the uterus of a human includes an outer guide member for insertion into a cervical canal of the human. The outer guide member includes a distal portion with an activatable seal for isolating the uterus from the external environment. The seal has a length in the range of about 3 to 8 mm, and the outer guide member defines a lumen having a longitudinal axis. The device also includes an inner catheter located within the lumen and slidable along the longitudinal axis of the lumen relative to the outer guide member. The catheter has a distal tip positionable distally of the seal to extend into the uterus. The inner catheter includes a fluid delivery lumen terminating at a distal fluid delivery port for delivering fluid into the uterus. The device defines a distal suction port for aspirating fluid and entrained blastocysts from the uterus. The device does not include an element for expanding the uterus.

In another general aspect, a device for recovering one or more blastocysts from the uterus of a human includes an outer guide member for insertion into a cervical canal of the human. The outer guide member includes a distal portion with an activatable seal for isolating the uterus from the external environment. The outer guide member defines a lumen having a longitudinal axis. The outer guide member is configured to be manipulatable by the operator to form a curvature along the longitudinal axis. The device also includes an inner catheter located within the lumen and slidable along the longitudinal axis of the lumen relative to the outer guide member. The catheter has a distal tip positionable distally of the seal to extend into the uterus. The inner catheter includes a fluid delivery lumen terminating at a distal fluid delivery port for delivering fluid into the uterus. The device defines a distal suction port for aspirating fluid and entrained blastocysts from the uterus.

In another general aspect, a system for recovering one or more blastocysts from the uterus of a human includes a device and a controller programmed to cyclically deliver lavage liquid to the uterus via the fluid delivery lumen and apply vacuum to the device from a vacuum source remote from the device. The device includes an outer guide member for insertion into a cervical canal of the human. The outer guide member includes a distal portion with an activatable seal for isolating the uterus from the external environment. The outer guide member defines a lumen having a longitudinal axis. The device also includes an inner catheter located within the lumen and slidable along the longitudinal axis of the lumen relative to the outer guide member. The catheter has a distal tip positionable distally of the seal to extend into the uterus. The inner catheter includes a fluid delivery lumen terminating at a distal fluid delivery port for delivering fluid into the uterus. The device defines a distal suction port for aspirating fluid and entrained blastocysts from the uterus.

Implementations may include one or more of the following features. For example, the controller may include a pump for delivering the lavage liquid and a pump for applying the vacuum.

In another general aspect, a process for recovering one or more blastocysts from the uterus of a human includes placing a device trans-vaginally into the cervical canal. The device includes an outer guide member and an inner catheter located within the outer guide member. The outer guide member includes a seal for isolating the uterus from the external environment. The process also includes advancing the inner catheter relative to the outer guide member positioning a distal region of the inner catheter within the uterus, delivering fluid through the inner catheter to the uterus, and applying a vacuum to the uterus to aspirate fluid and entrained blastocysts from the uterus.

Implementations may include one or more of the following features. For example, placing the device may include locating the seal in the cervical canal. Locating the seal may include locating the seal between the internal cervical os and the external cervical os such that the seal does not extend into the vagina or the uterus.

In another general aspect, a process for recovering one or more blastocysts from the uterus of a human includes placing a device trans-vaginally into the cervical canal and cyclically delivering fluid through the device to the uterus and applying a vacuum to the uterus to aspirate fluid and entrained blastocysts from the uterus without introducing air into the uterus.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
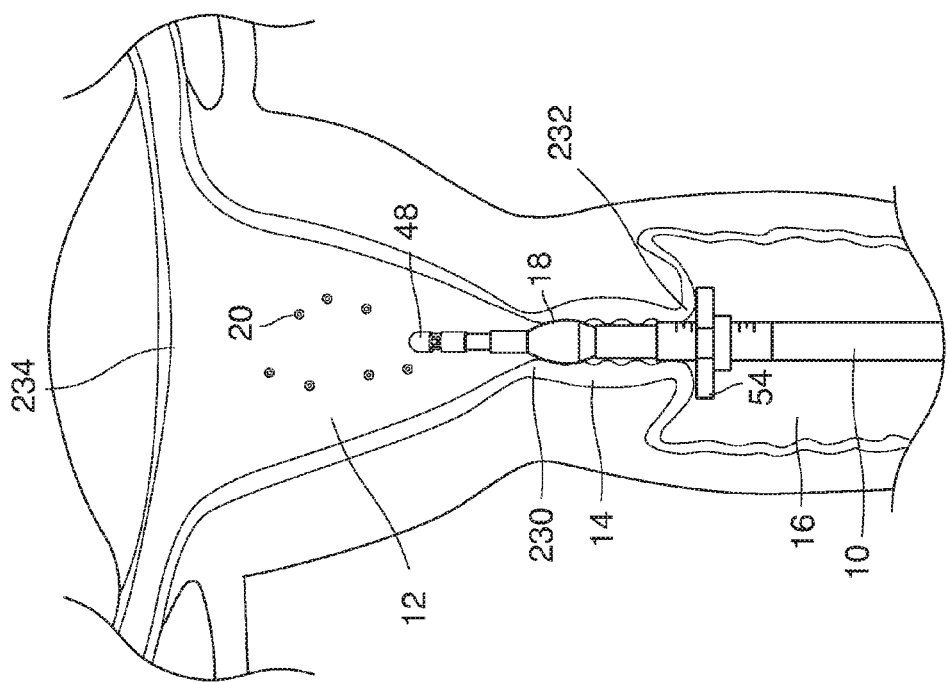
FIG. 1 is a side view of a lavage device within a female reproductive tract.

Uterine lavage is performed to withdraw in vivo fertilized preimplantation embryos from a woman. The preimplantation embryos are produced, for example, by superovulation and artificial insemination. Referring to FIG. 1, to perform the uterine lavage, a lavage device 10 is inserted into the uterine cavity 12 via the cervical canal 14 and the vagina 16. The uterine cavity 12 is sealed from the external environment by an activatable seal, for example, an inflatable balloon collar 18 of the lavage device 10, and lavage is performed by introducing fluid into the uterine cavity 12 and withdrawing fluid and entrained preimplantation embryos, i.e., blastocysts 20, from the uterine cavity 12.

Figure 2:
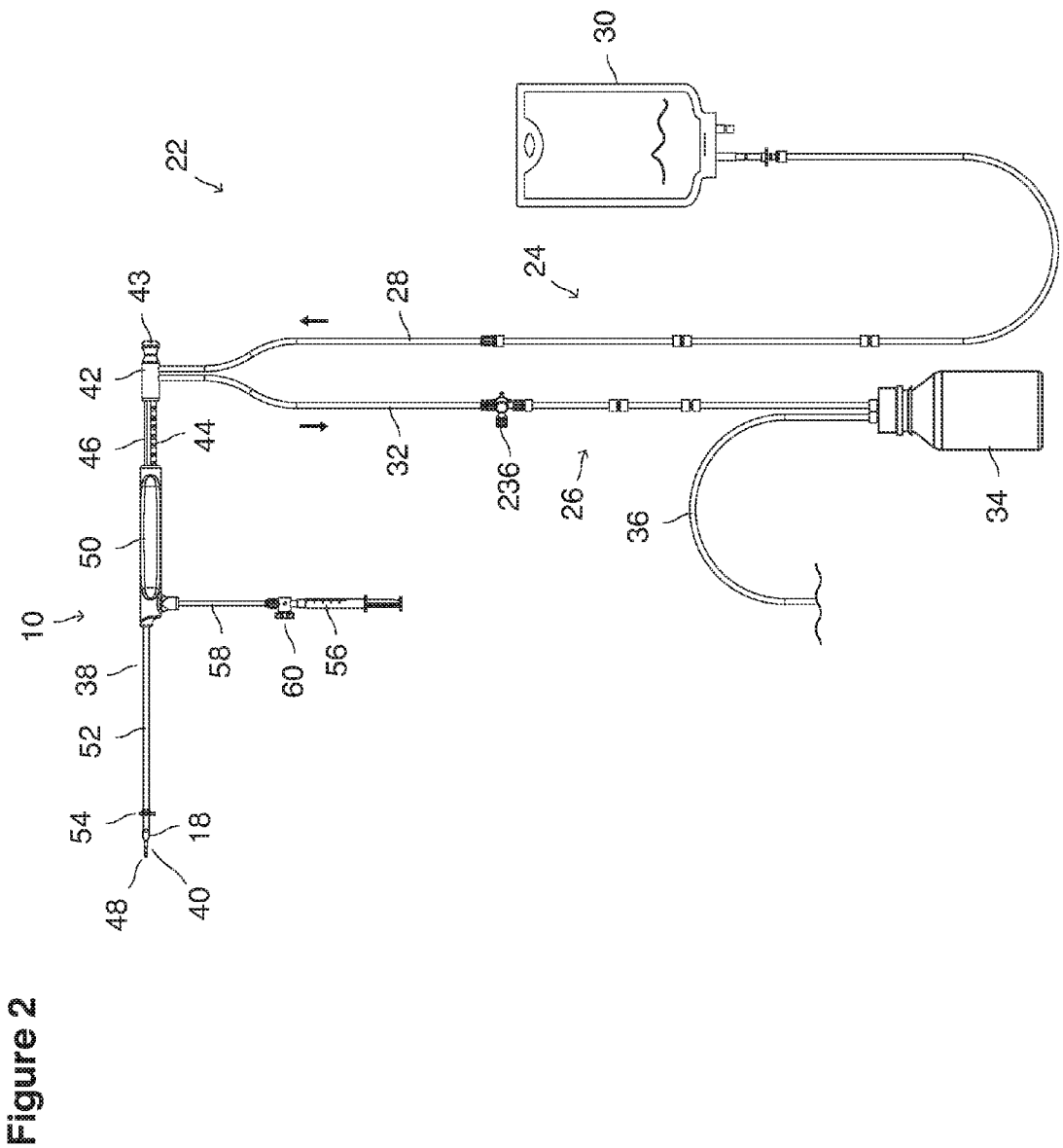
FIG. 2 is a side view of the lavage device.

Referring to FIG. 2, a uterine lavage system 22 includes the lavage device 10, an inflow section 24, and an outflow section 26. The inflow section 24 includes a fluid supply line 28 attached to a fluid bag 30, and the outflow section 26 includes a suction recovery line 32 attached to an embryo recovery trap 34, which is attached to a suction line 36. The lavage device 10 includes an outer, formable guide member 38 and an inner catheter 40 slidably received within the outer guide member 38.

The inner catheter 40 includes a manifold 42 to which the fluid supply line 28 and the suction recovery line 32 are attached. The manifold 42 has a control knob 43 for manipulating the inner catheter 40, and extending distally from the manifold 42, the inner catheter 40 includes a stabilizing bar 44, a supply/suction line 46, and an atraumatic tip 48. The outer guide member 38 includes a handle 50, a guide arm 52, a cervical stop 54, and a seal, for example, the balloon collar 18. The balloon collar 18 is inflated using air or liquid delivered by a supply syringe 56 through a supply line 58 attached to the handle 50. Fluid flow through supply line 58 is controlled by a stopcock 60.

Figure 3A:
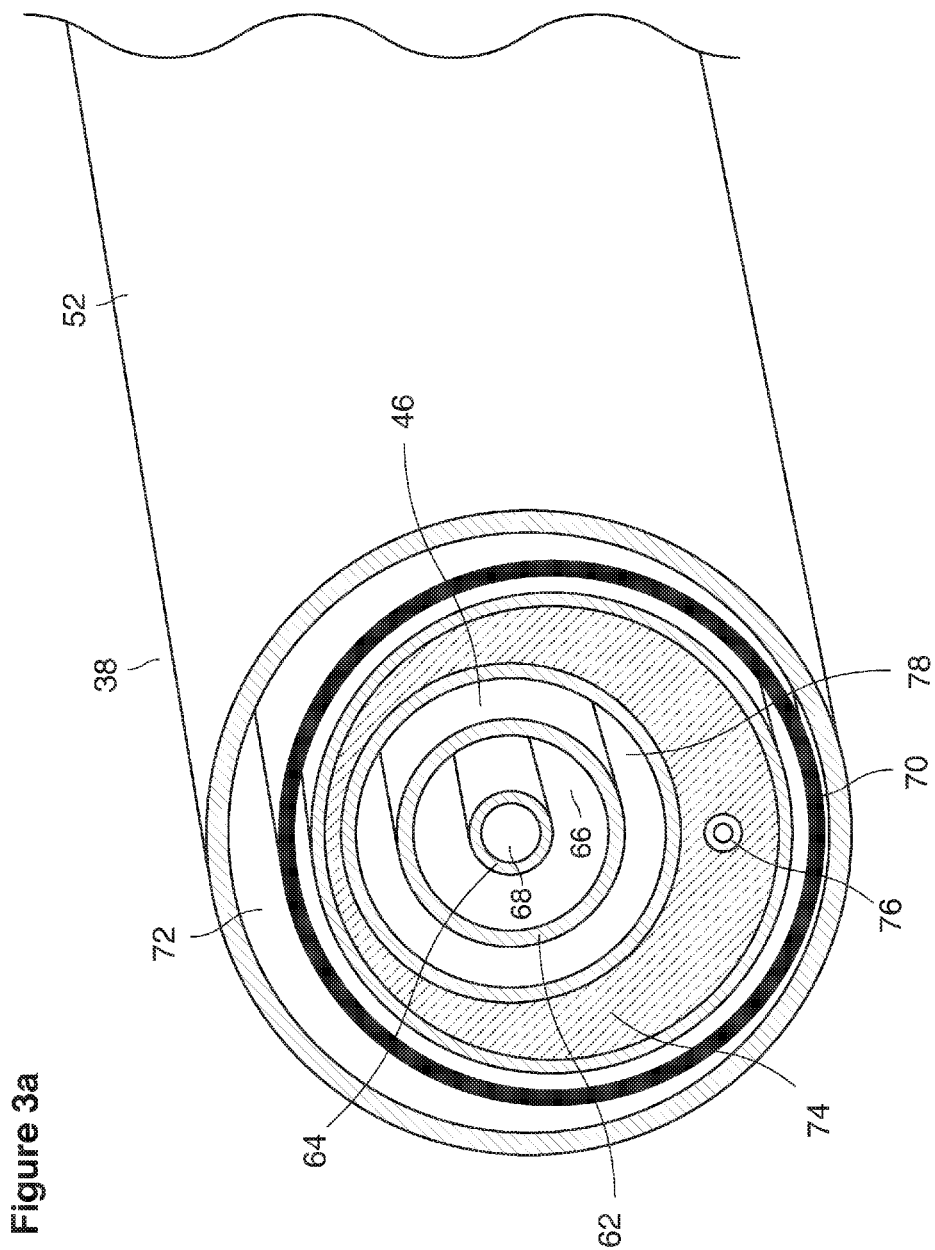
FIGS. 3a and 3b are cross-sectional views of portions of the lavage device.
Figure 3B:
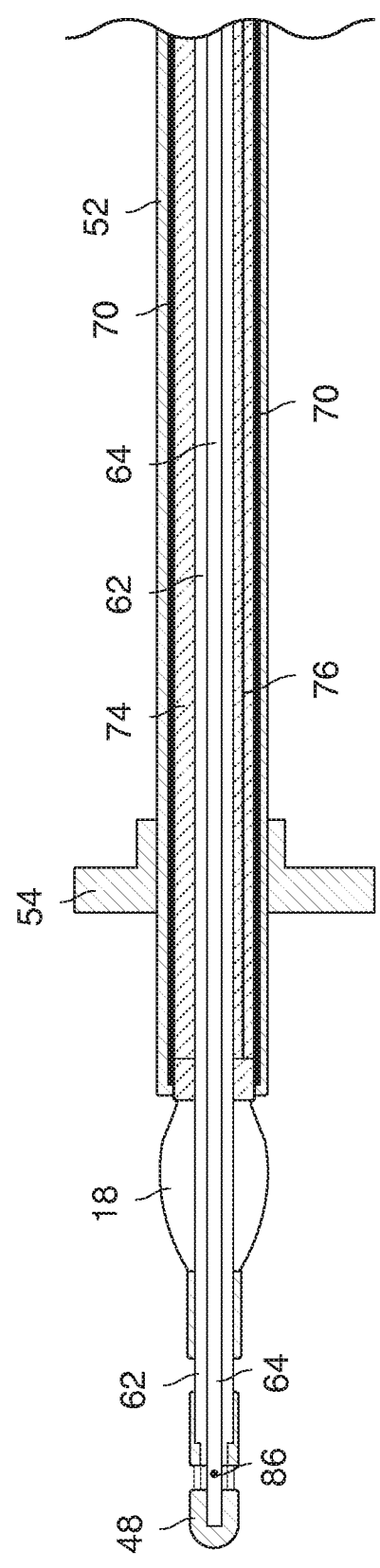
Figure 4:
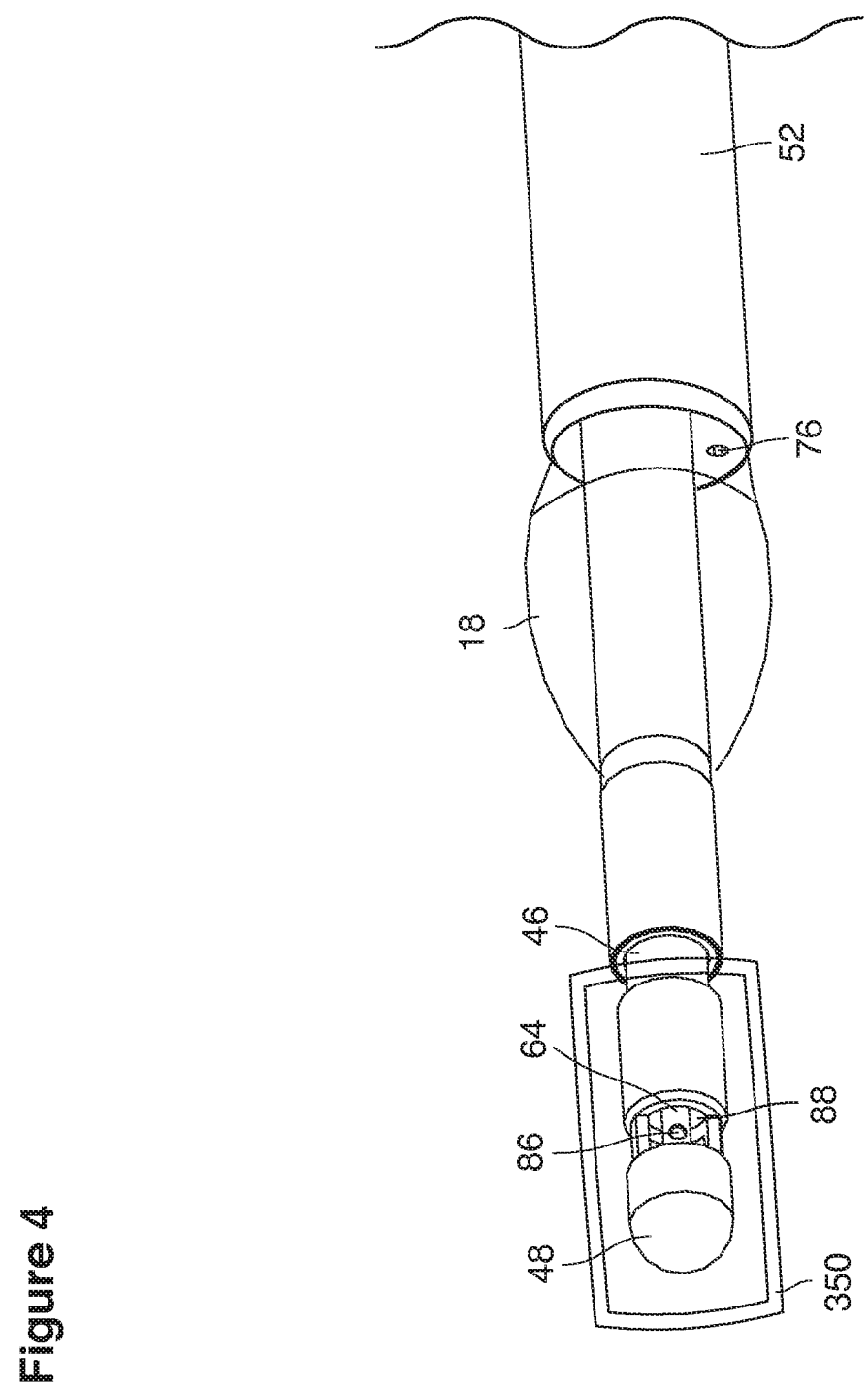
FIG. 4 is a close-up perspective view of a distal portion of the lavage device.

Referring to FIGS. 3A and 3B, the supply/suction line 46 of the inner catheter 40 is a coaxial tube including an outer tubular member 62 and an inner tubular member 64. Defined between the tubular members 62, 64 is an outflow lumen 66 for aspiration of fluid and entrained blastocysts from the uterine cavity, and the inner tubular member 64 defines an inflow lumen 68 for delivery of lavage fluid to the uterine cavity. The outer guide member 38 includes a formable tube 70 located within a lumen 72 of the guide arm 52. The formable tube 70 surrounds a support member 74, which defines a lumen 76 connected to the balloon inflation supply line 58. FIG. 4 shows the termination of the supply lumen 76 at the balloon collar 18. Support member 74 defines a lumen 78 (FIG. 3A) that receives the supply/suction line 46 of the inner catheter 40.

Figure 5:
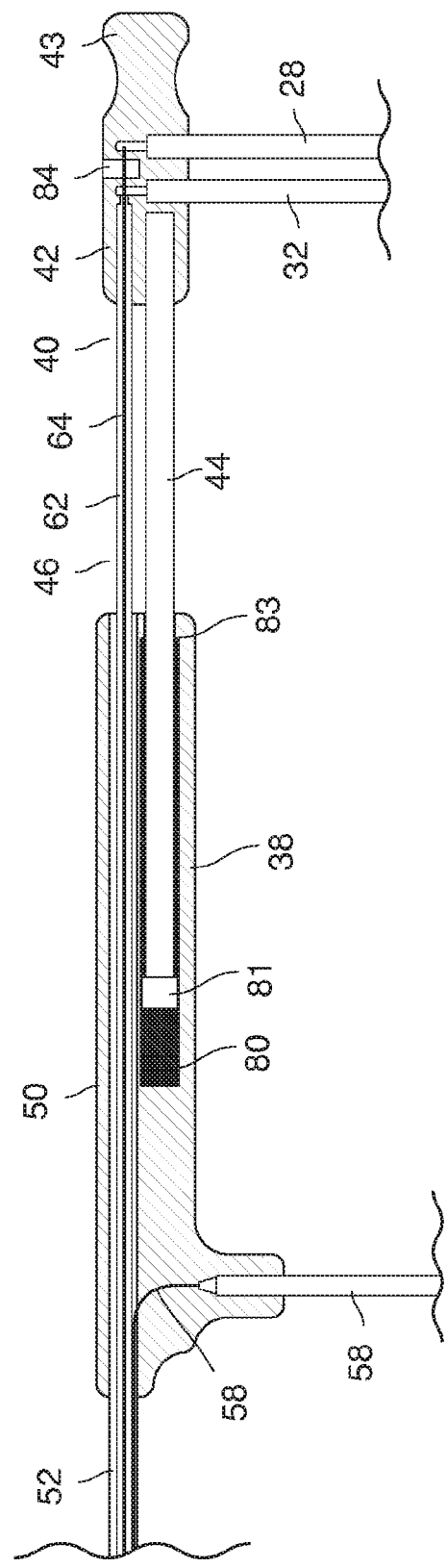
FIG. 5 is a side cross-sectional view of a handle portion of the lavage device.
Figure 6:
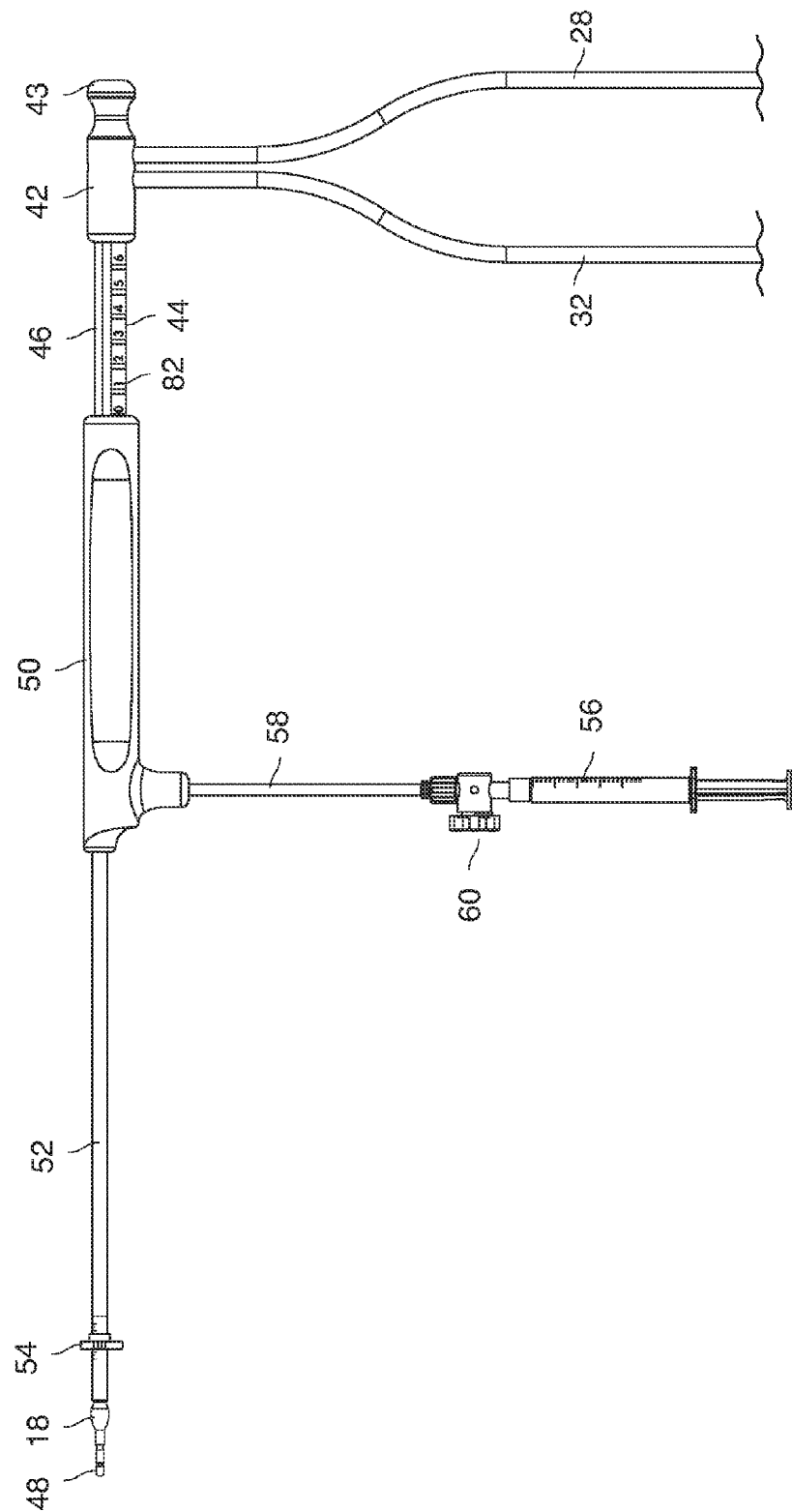
FIGS. 6 and 7 are side and top views of the lavage device in a retracted position.
Figure 7:
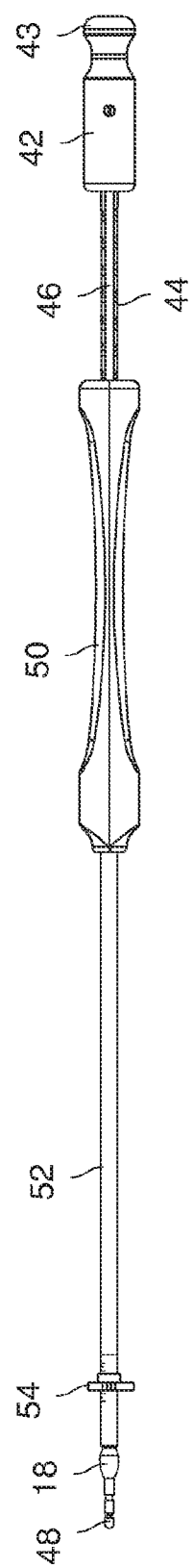
Figure 8:
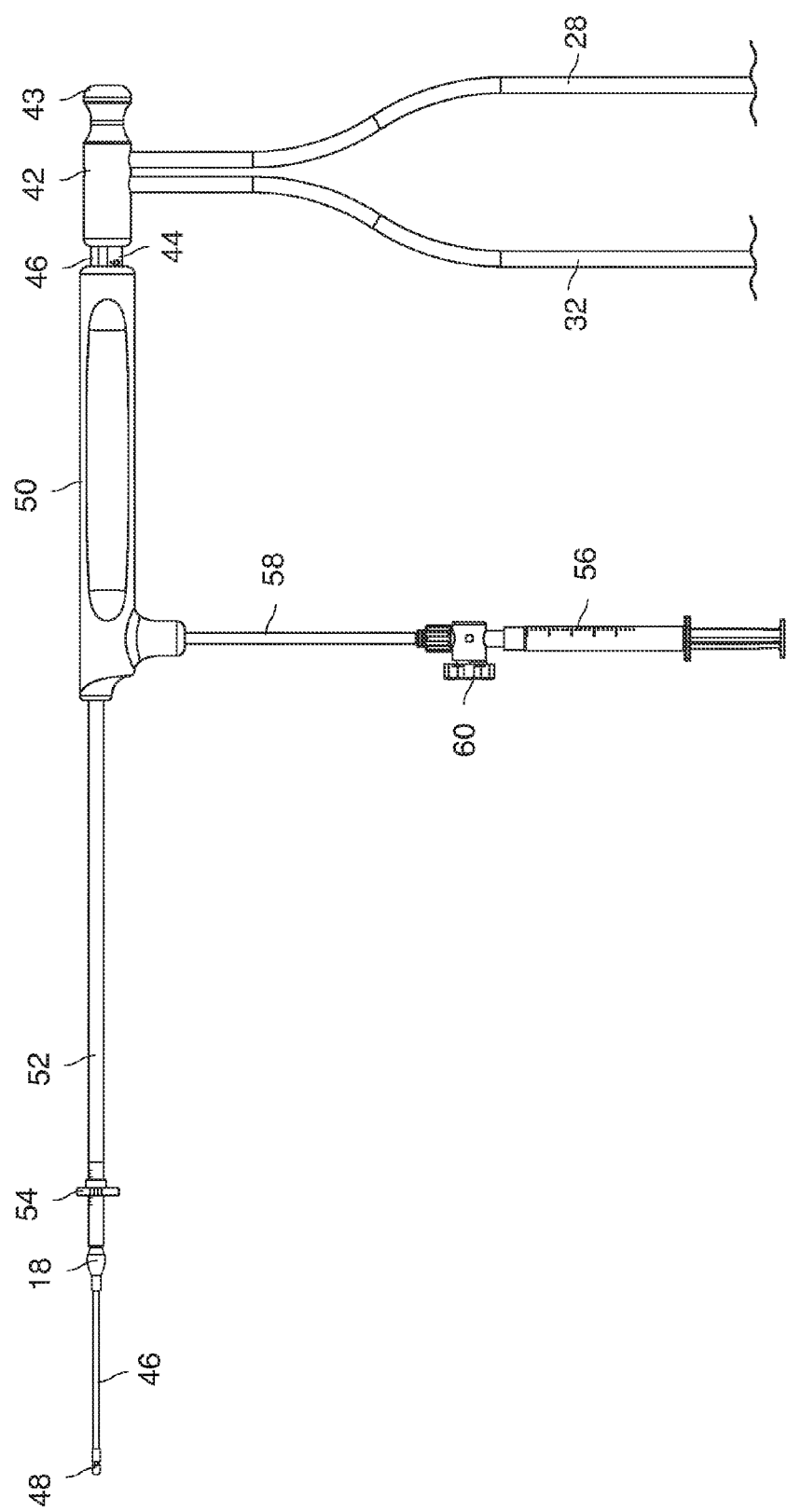
FIG. 8 is a side view of the lavage device in an extended position.

Referring to FIG. 5, the handle 50 defines a slot 80 that receives the stabilizing bar 44. When the inner catheter 40 slides axially relative to the outer guide member 38, the stabilizing bar 44 slides along the slot 80. The stabilizing bar 44 helps support the manifold 42. As illustrated in FIG. 6, the stabilizing bar 44 includes indicia 82 that indicate the extent of insertion of the inner catheter 40 relative to the outer guide member 38. The inner catheter 40 can be moved axially between the retracted position of FIGS. 6 and 7, and the extended position of FIG. 8. The stabilizing bar 44 terminates in a head 81 and the handle 50 includes a stop 83 which prevents the head 81 from exiting from the slot 80 such that the inner catheter 40 and the outer guide member 38 are permanently joined to form a single, integrated device, i.e., the supply/suction line 46 cannot be completely removed from the outer guide member 38 by the operator.

Referring again to FIG. 5, the inner tubular member 64 of supply/suction line 62 is supported by a resin block 84 in manifold 42.

Figure 9A:
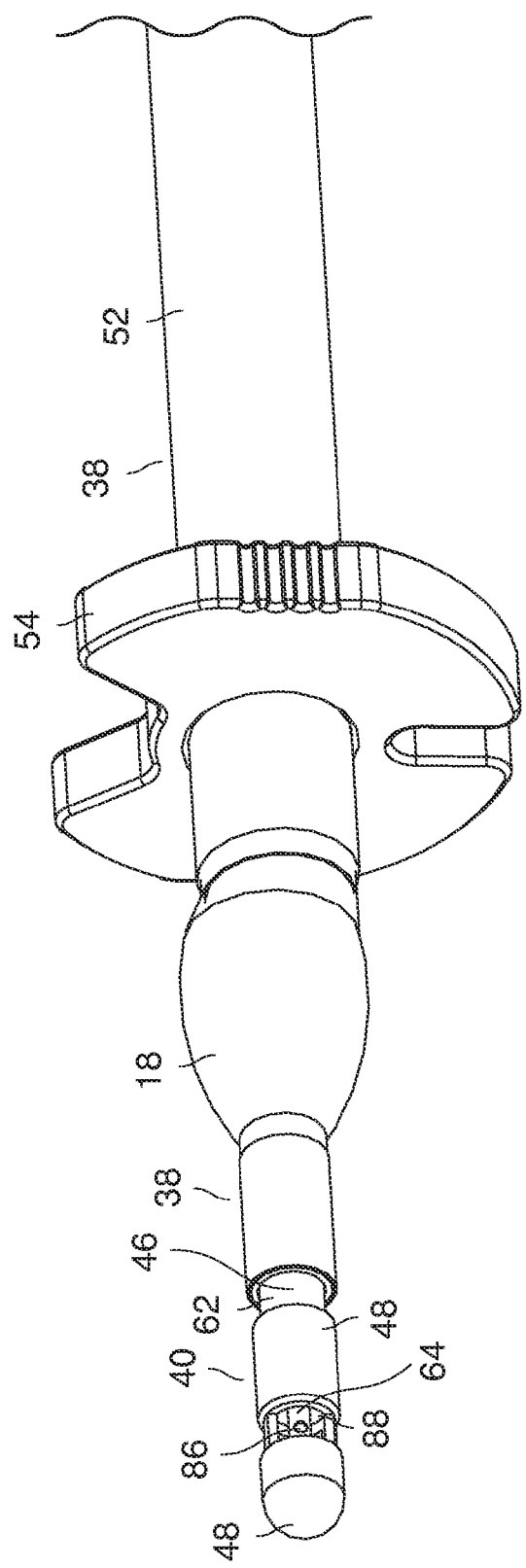
FIG. 9a is a close-up perspective view of a distal portion of the lavage device.
Figure 9B:
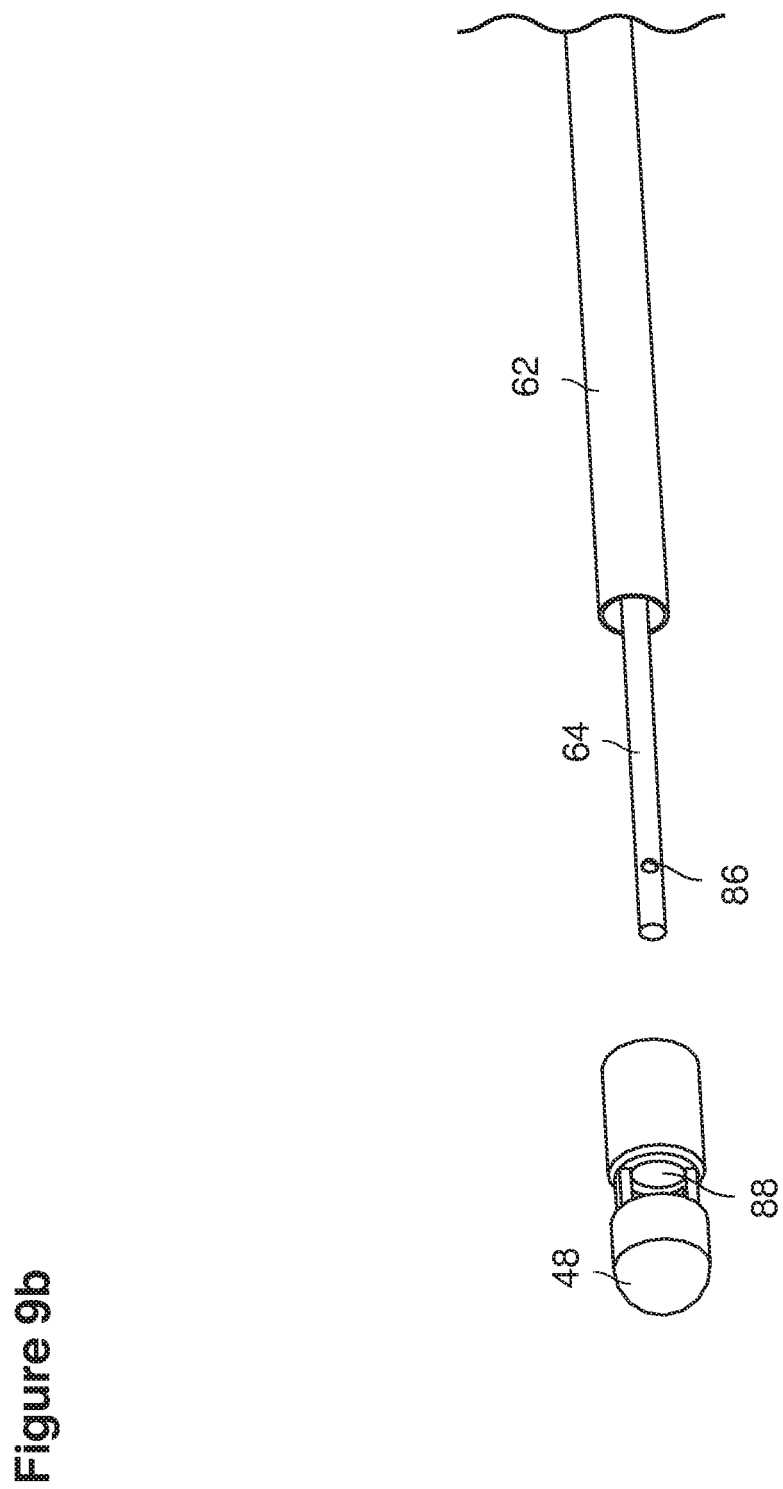
FIG. 9b is an exploded view a distal portion of the lavage device.
Figure 10:
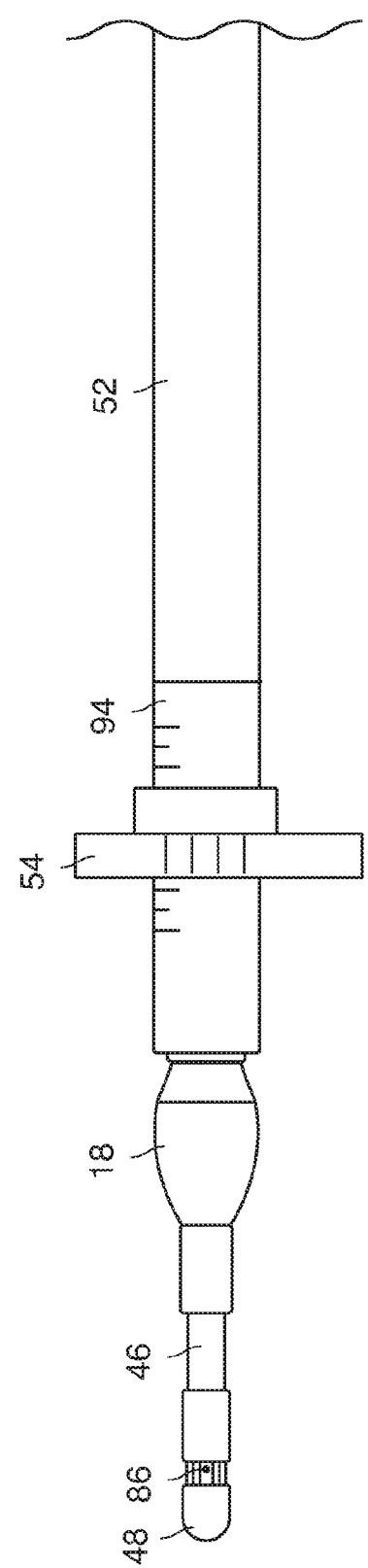
FIG. 10 is a side view of the lavage device.

Referring to FIGS. 9A, 9B and 10, the inner tubular member 64 of the supply/suction line 46 defines a fluid supply line port 86, for example, two diametrically opposed ports, through which fluid is delivered to the uterine cavity. The ports can be non-circular in shape to provide directional control of fluid spray. For example, the proximal side of the port can be perpendicular to the longitudinal axis of the inner tubular member 64 and the distal side of the port can diverge from the axis at an obtuse angle. The outer tubular member 62 of the supply/suction line 46 terminates proximal of port 86 and the atraumatic tip 48 defines fluid suction line ports 88 that are in fluid communication with outflow lumen 66 through which fluid and entrained blastocysts 20 are recovered from the uterine cavity. The position of the suction line ports 88 about fluid supply line port 86 avoids plugging of the suction recovery line port 88 with mucous.

As shown in FIG. 4, the lavage device 10 includes a priming cap 350 that is used to cover the ports 86 and 88 providing a seal to allow priming of the device prior to use.

Figure 11:
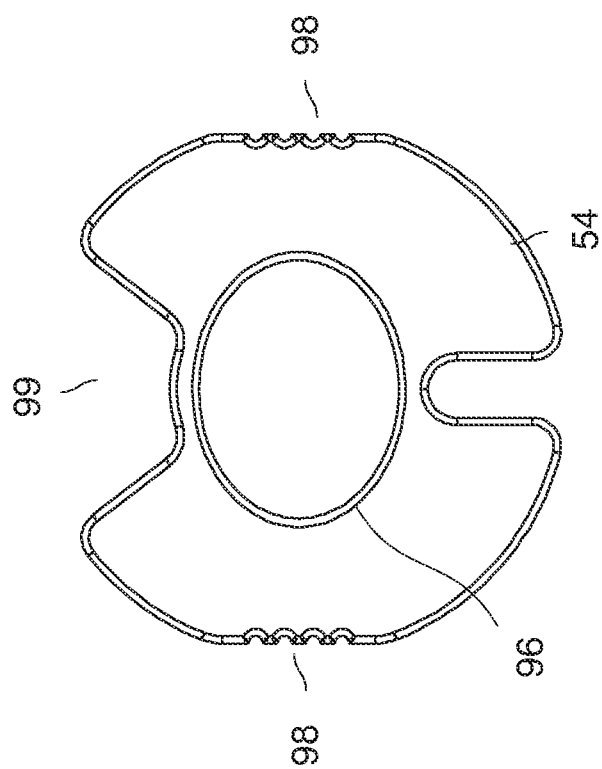
FIG. 11 is a front view of a cervical stop of the lavage device.

The position of the cervical stop 54 is adjustable relative to the balloon collar 18 along a cervical stop scale 94 (FIG. 10) on the guide arm 52. The position of the cervical stop 54 defines a dimension corresponding to a distance from an opening of the cervix at the vagina (the external cervical os) and an opening of the cervix at the uterus (the internal cervical os). The cervical stop 54 can be clamped in a set position along the guide arm 52. Referring to FIG. 11, the cervical stop 54 includes a locking ring 96 and flange adjustment grips 98. In its rest state, the locking ring 96 is not circular in shape and has an inner dimension smaller than the outer diameter of the guide arm 52 to lock the cervical stop 54 in position. By squeezing in on the flange adjustment grips 98, the operator can deform the shape of the locking ring 96 to a more circular shape that can slide along the guide arm 52 to adjust the position of the cervical stop 54. Upon release of the squeezing force, the locking ring 96 returns toward it rest state, locking the cervical stop 54 in place. The cervical stop 54 is shaped to have a visual port 99 that allows the operator to see the cervix and align the atraumatic tip 48 during insertion of the uterine device 10. The cervical stop scale 94 is etched into the outside of the catheter guide arm 52 and marks the position of the cervical stop when it is custom-adjusted to each patient prior to insertion.

Figure 12:
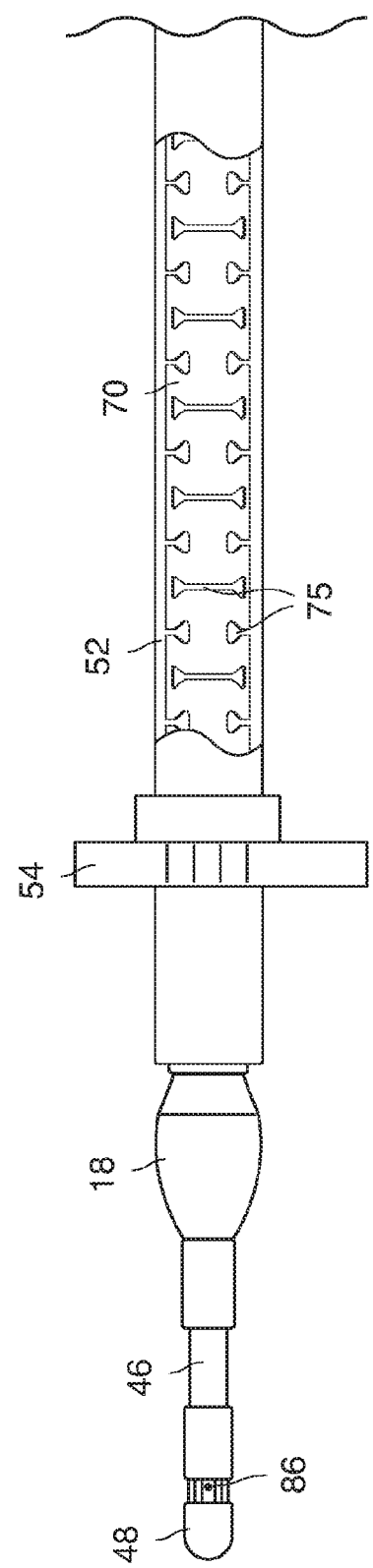
FIGS. 12-14 are partially cut side views of the lavage device.
Figure 13:
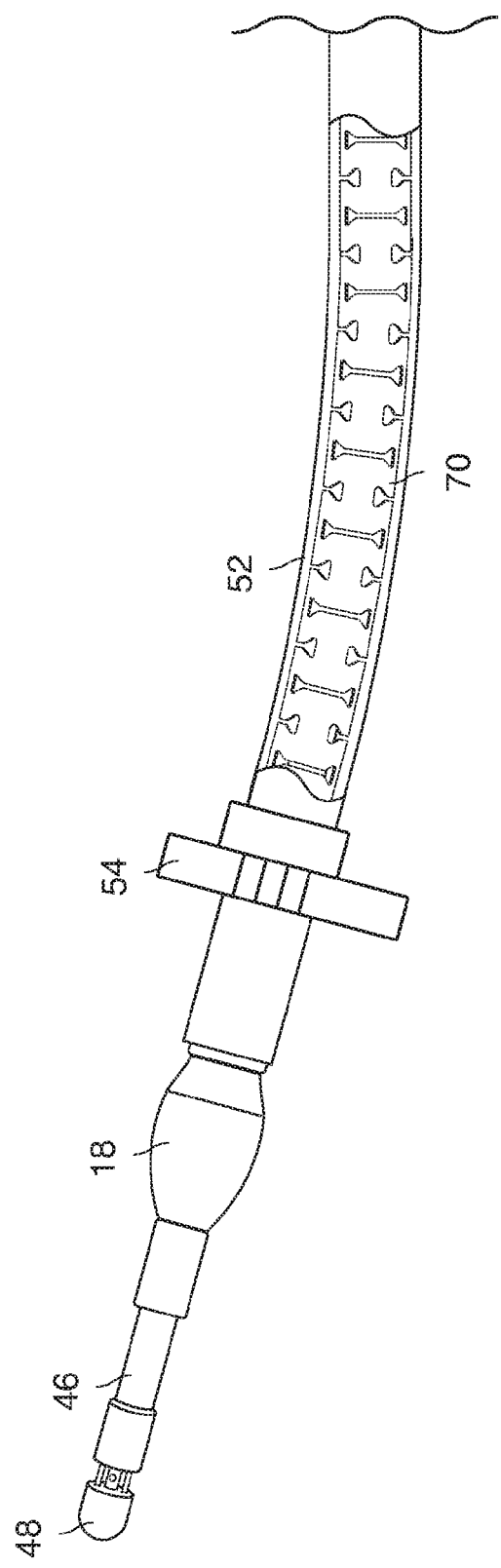
Figure 14:
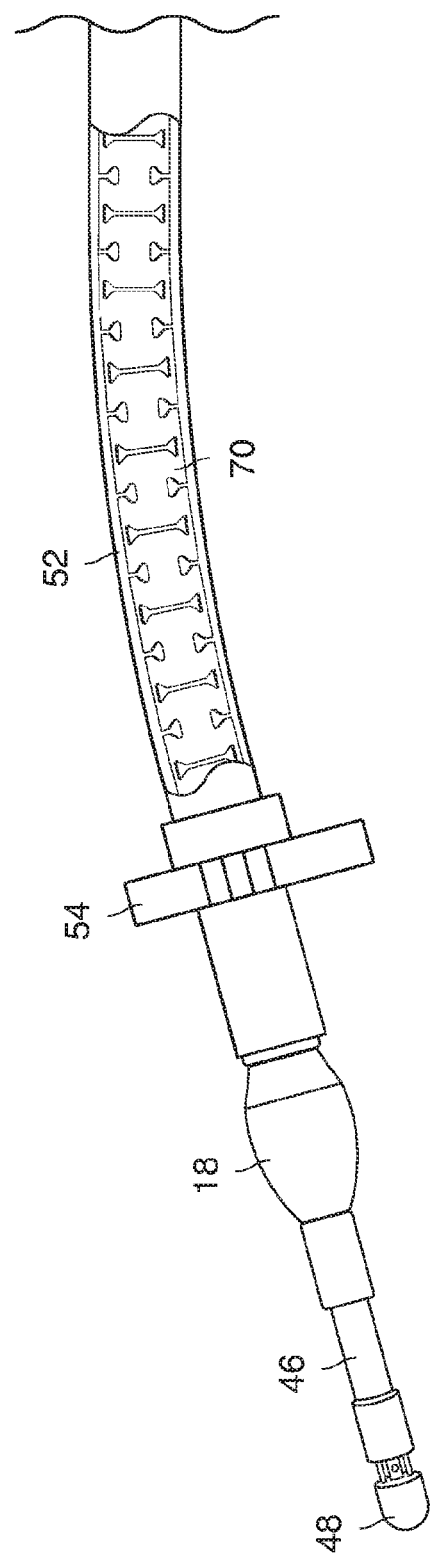

Referring to FIGS. 12-14, the formable tube 70 can be bent into a desired position by the operator to allow the atraumatic tip 48 and the supply/suction line 46 of the lavage device 10 to travel through the cervical canal and into the cervix with minimal discomfort to the patient. The angle can be preset from about 0 to 60 degrees and is customized to individual women in order to accommodate the different anatomical variations of the uterine flexion. FIG. 13 shows the formable tube 70 modified to 30 degrees up, and FIG. 14 shows the formable tube 70 modified to 30 degrees down. The formable tube 70 is made, for example, from Stainless Steel, is coated with polyamide, and includes cut-outs 75.

The outer guide member 38 has an outer diameter in the range of, for example, 6-7 mm, and is made from, for example heat shrink polyolefin or p-bax elastomeric over layer. Inner catheter 40 has an outer diameter in the range of, for example, 3-6 mm, and for example, 3.05 mm, and is made, for example, from stainless steel. Cervical stop 54 has a diameter of, for example, 19.05 mm and is made, for example, from polyamide. The lavage device 10 is sized for use without anesthesia.

Figure 15:
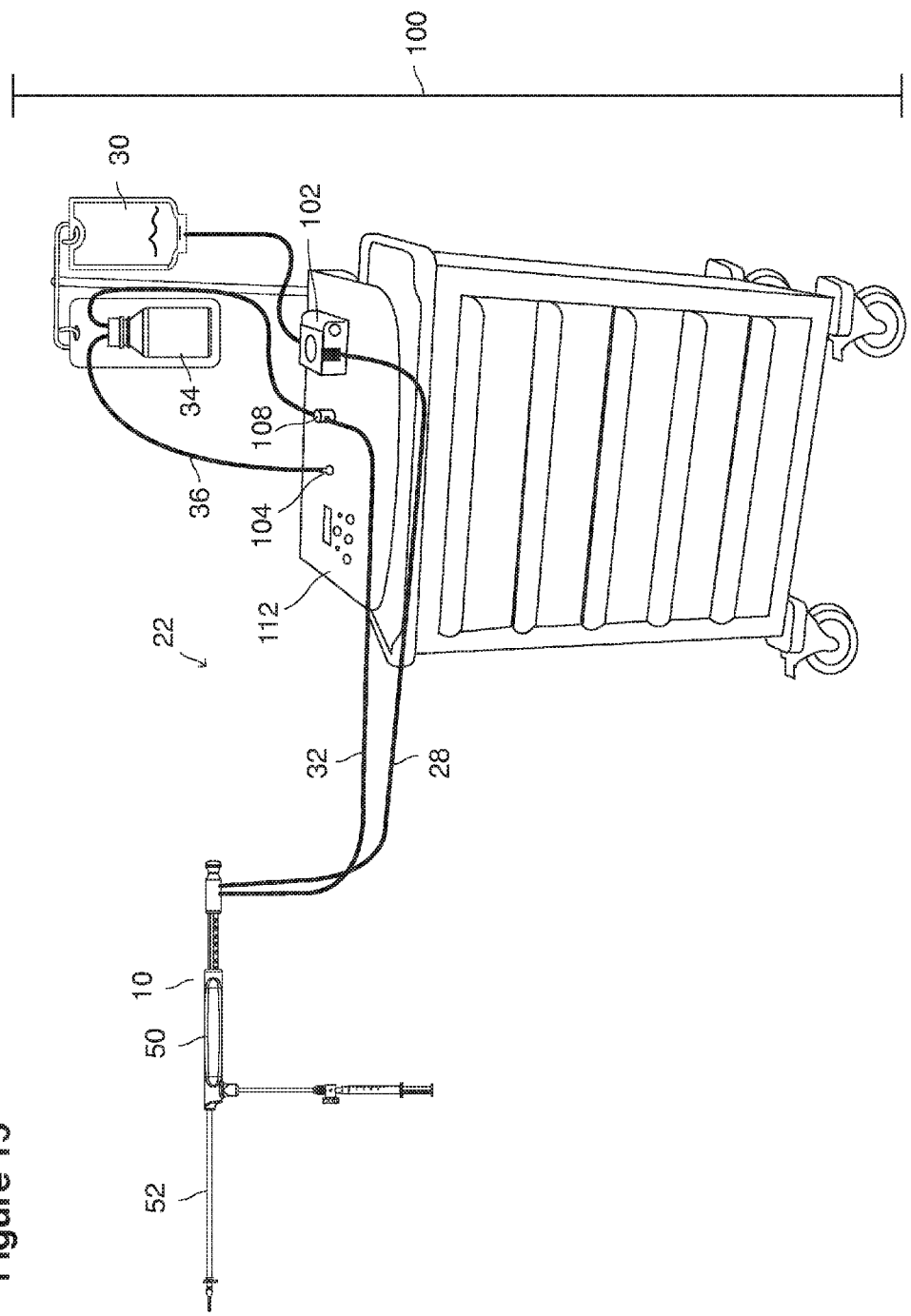
FIG. 15 illustrates the lavage device connected to a control cart.
Figure 16:
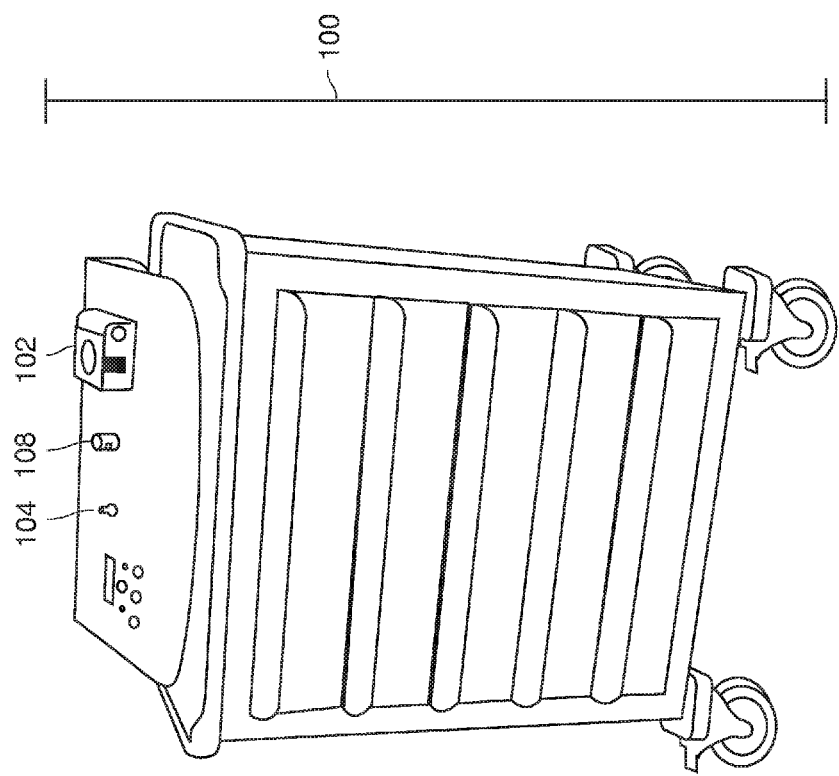
FIG. 16 is an enlarged view of the control cart.

Referring to FIGS. 15 and 16, the uterine lavage system 22 includes a control cart 100 used to connect the lavage device 10 to the lavage fluid bag 30 and the embryo recovery trap or collection bottle 34, and to control the inflow of fluid to the uterine cavity and the removal of fluid and entrained blastocysts from the uterine cavity. The lavage fluid bag 30 is supported by the cart 100, and the supply line 28 is routed from the fluid bag 30 through a peristaltic fluid pump 102 to the lavage device 10. Blastocysts 20 are recovered through the lavage device 10 and travel to the collection bottle 34 via the suction recovery channel 32. The collection bottle 34 is connected to a vacuum supply connector 104 via the suction line 36 through which suction is applied to suction recovery channel 32. The application and level of suction is controlled by a pinch valve 108. The introduction of fluid is controlled by the pump 102. The lavage fluid is drawn from the bag 30, pumped through the supply line 28, and pulsed in and out of the uterus through the atraumatic tip 48. The pump 102 supplies uterine lavage fluid in a pulse rhythm with a vacuum element that alternates suction and pulses cadenced the opposite to the fluid delivery at a preset frequency of, for example, 0.5 to 4.0 seconds with less fluid being aspirated than delivered to ensure that air is not introduced into the uterine cavity.

The control system manages pulse and flow via electromechanical means (software instructs the control system in use of vacuum and pulse of fluid delivery). The control system is reprogrammable such that software can be loaded that alters the pulse frequency, the pressure of fluid supply, the frequency of vacuum pressure, amount of vacuum supplied, and the frequency and duration of pause steps between pressure and vacuum supply.

Figure 17:
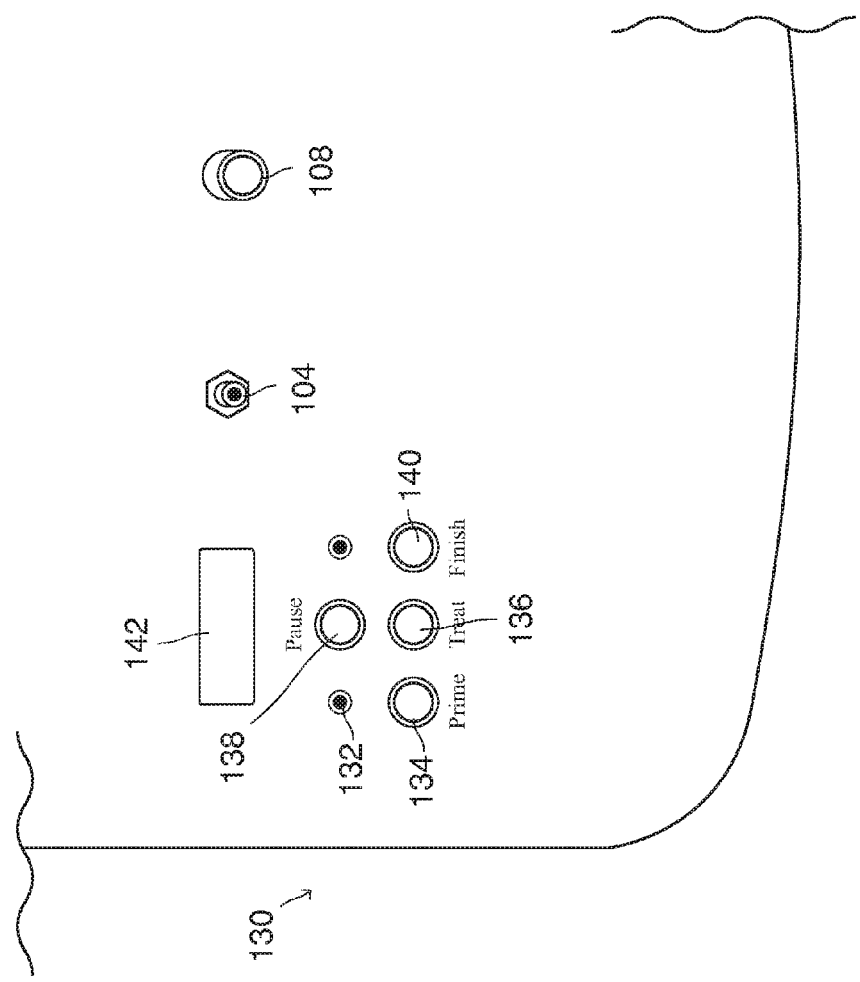
FIG. 17 is a view of a controller interface portion of the control cart.

Referring to FIG. 17, a user interface 130 for controlling the system 22 includes a power button 132, a prime button 134, a treat button 136, a pause button 138, and a finish button 140. The power on/off button turns on an electrical power supply to the control system. The Prime button starts the fluid supply pump and keeps the pump running for the duration of the time that the button is depressed. The Treat Button starts the lavage cycle invoking the software to execute a pattern of pulse-pause-vacuum-pause until the fluid supply is utilized fully. The Finish button stops the lavage cycle. Faults in the set-up of the lavage device or with the software during the lavage cycle are indicated on a LED screen 142 and the control system automatically pauses the lavage cycle until the problem is resolved. The user interface 130 produces a series of electronic beeps indicating when a portion of the lavage cycle is completed. Beeps occur after each treat cycle and after the finish cycle is completed.

The IV bag 30 is a standard format, latex free, PVP free, DEHP free IV bag that can hold requisite lavage fluid solutions. The IV bag holds no more than the total amount of lavage fluid to be used in the lavage cycle. The IV bag is attached to the lavage system via a standard spike and tube format. The IV bag is translucent such that the operator can monitor fluid movement from the IV bag though the tubing and the catheter.

Figure 18:
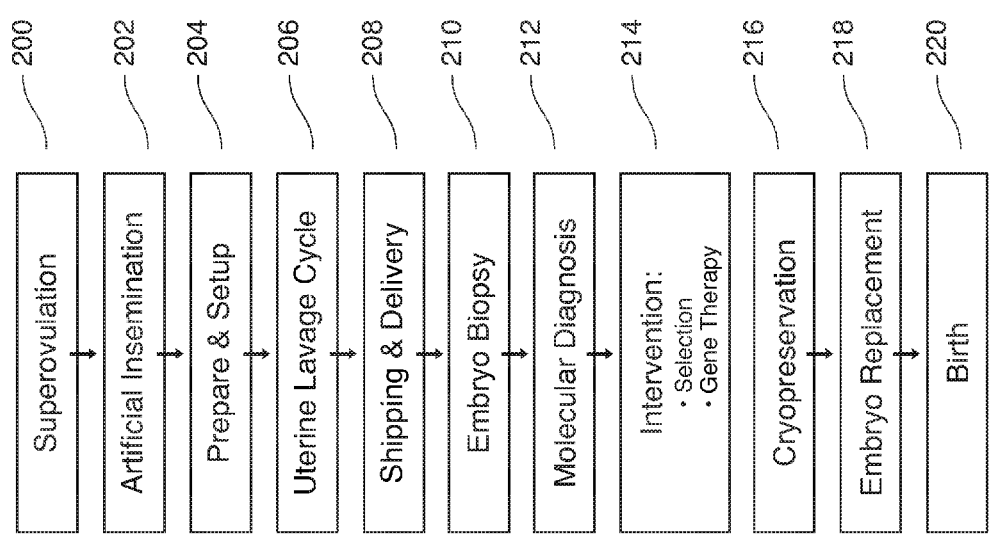
FIG. 18 is a flow chart illustrating an example process that uses a lavage system.

Referring to FIG. 18, the lavage system 22 is used in one or more steps of a procedure that includes superovulation 200, artificial insemination 202, preparation and set up 204, uterine lavage cycle 206, shipment and delivery of blastocysts recovered during the lavage process 208, shutdown cycle 222, embryo biopsy 210, molecular diagnosis 212, intervention 214, cryopreservation 216, embryo replacement 218, and ending in the birth 220 of a healthy baby.

Preparatory to lavage, prior to superovulation and insemination, a practice lavage can be performed (approximately one or two months) before the live procedure is scheduled. In the practice lavage, measurements are taken (with the assistance of imaging technologies) and the lavage device 10 is custom fit to enable the anatomy of each patient to be accommodated. Precise imaging of each woman's anatomy utilizes imaging devices, for example, two-dimensional or three-dimensional ultrasound, magnetic resonance imaging, or other imaging technology. The operator determines the optimal position for cervical stop 54 and records the reading on the scale 94, the optimal insertion of stabilizing bar 44 and records the reading on the indicia 82, the angle the lavage device is to be set at by modification of the formable tube 70, and the amount of inflation of the balloon collar 18 to accommodate the degree of cervical dilation of the patient.

Superovulation is caused in a woman to form multiple corpora lutea that undergo apoptosis and cannot support development of a viable implanted pregnancy following shutdown 222. In-vivo fertilization of multiple oocytes by artificial insemination and/or natural insemination is followed by maturation of the fertilized oocytes to form multiple mature preimplantation embryos that present to the uterine cavity as blastocysts.

To cause superovulation, FSH is delivered to the woman's body. The FSH can be delivered by self-injection. The dosage of FSH is appropriate for induction of superovulation, in vivo fertilization, and embryonic maturation. The FSH is, for example, self-injected daily for 5 to 15 days in the range of 5 to 600 mIU per day. The FSH includes at least one of injectable menotropins containing both FSH and LH; purified FSH given as urofollitropins; recombinant pure FSH; or single doses of long acting pure FSH (recombinant depot FSH), including administering GnRH antagonists to quiet the ovaries while causing superovulation. The GnRH antagonists include receptor blocker peptides. The GnRH antagonists include at least one of Cetrotide 0.25 to 3.0 mg, Ganirelix, Abarelix, Cetrorelix, or Degarelix in which causing superovulation includes administering GnRH including administering a single dose of hCG agonist subcutaneously or snuffed to trigger the superovulation. The GnRH includes at least one of Leuprorelin, Leuprolide acetate, Nafarelin, or Naferelin acetate snuff 117 including administering LH or hCG without GnRH agonist including administering LH or hCG or in combination with GnRH agonist in which impaired (apoptosis) corpus luteum estradiol and progesterone production is supplemented to maintain embryonic viability and maturation by including administrating progesterone and estradiol until recovery of the blastocysts. The progesterone includes at least one of vaginal progesterone, or oral progesterone and the estradiol includes at least one of oral or transdermal estradiol. The progesterone includes Crinone® 1 application per day or Prometrium 200 mg® 3 applications per day or Prometrium 200 mg® 3 oral capsules per day, and the estradiol includes transdermal estradiol patches 400 ug per day or oral estradiol 0.5 to 5.0 mg per day in which blastocyst implantation is prevented by discontinuing administration of estradiol and progesterone starting on the day of blastocysts recovery on the day of lavage. Desynchronization includes administering progesterone receptor antagonist. The administering includes a single dose of progesterone receptor antagonist (Mifepristone 600 mg) injected into the uterine cavity with a second dose (Mifepristone 600 mg) mg given by mouth one day prior to expected menses. Desynchronization includes administering GnRH antagonist on the day on which the blastocysts are recovered to induce further corpus luteum apoptosis, suppress luteal phase progesterone, and further decrease risk of a retained (on account of blastocysts missed by the intrauterine lavage) pregnancy. The GnRh antagonist includes Cetrotide 0.25 to 3.0 mg.

Figure 19:
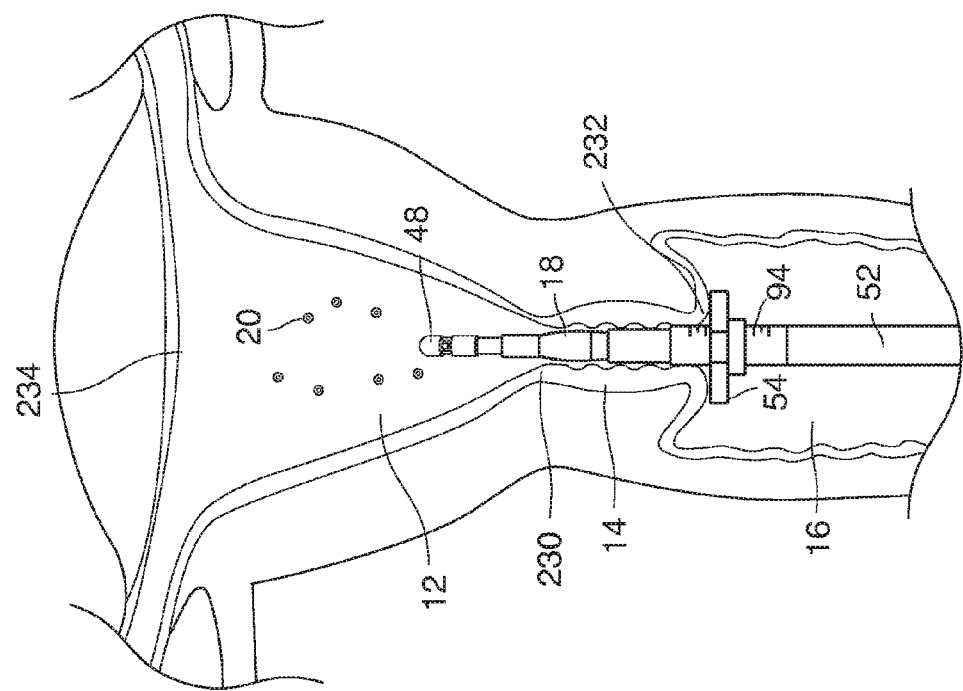
FIGS. 19-29 illustrate a lavage process using the lavage device.

Uterine lavage is typically performed between 4 and 8 days after the LH dose or LH surrogate trigger that released in vivo the multiple oocytes resulting from the superovulation. Referring to FIG. 19, at the optimal time (most likely day 6), the blastocysts 20 are located between the anterior and posterior uterine walls at approximately the geometric center of the uterine cavity 12. This location is in close proximity to the ultimate site of implantation, which is believed would take place within one day or less after the procedure if the blastocysts 20 were not recovered.

In preparation for the live lavage, the disposable and reusable elements of the instrument are selected based on the prior measurements and study of the woman's anatomy, and assembled and attached to the pulsing and suction elements, ready for the procedure. The operator sets the cervical stop 54 at the position determined on the cannula that ensures the balloon collar 18 is positioned along the internal cervical os 230. The cervical stop 54 is set relative to the measurement markings on the cervical stop scale 94 that defines the distance from the balloon collar 18, which has been premeasured by the device operator, and is clamped to the catheter guide arm 52.

The operator then shapes the catheter guide arm 52 as predetermined by the operator such that when the lavage device 10 is placed into the uterus the atraumatic tip 48 is positioned for extension along the midline of the uterus. The catheter guide arm 52 is flexible and will hold its shape via internal formable tube 70, and is bent into position to accommodate the position of the uterus relative to the particular woman's body (anteverted, retroverted, cast medially or laterally or any combination therein). The anatomy of the patient in question has been documented in prior exams such that the uterus position information can be used to prepare the lavage device for the uterine lavage cycle.

Temperature preparations are completed such that prior to the lavage cycle the fluid bag 30 with lavage fluid is preheated to 37 degrees Celsius by placing the fluid bag on a heating plate for a period of 30 minutes. The embryo recovery trap 34 is preheated for 30 minutes by placing a heating wrap around the container. This step ensures that the blastocysts 20 will be sustained at 37 C for the time period just after removal from the uterus through the arrival at an embryology laboratory.

Figure 20:
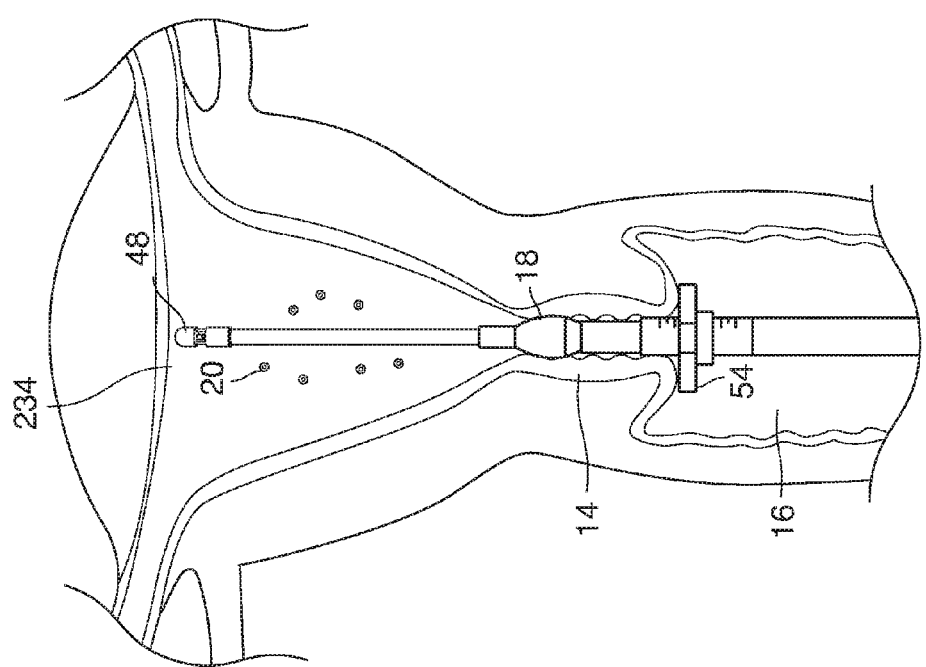
Figure 21:
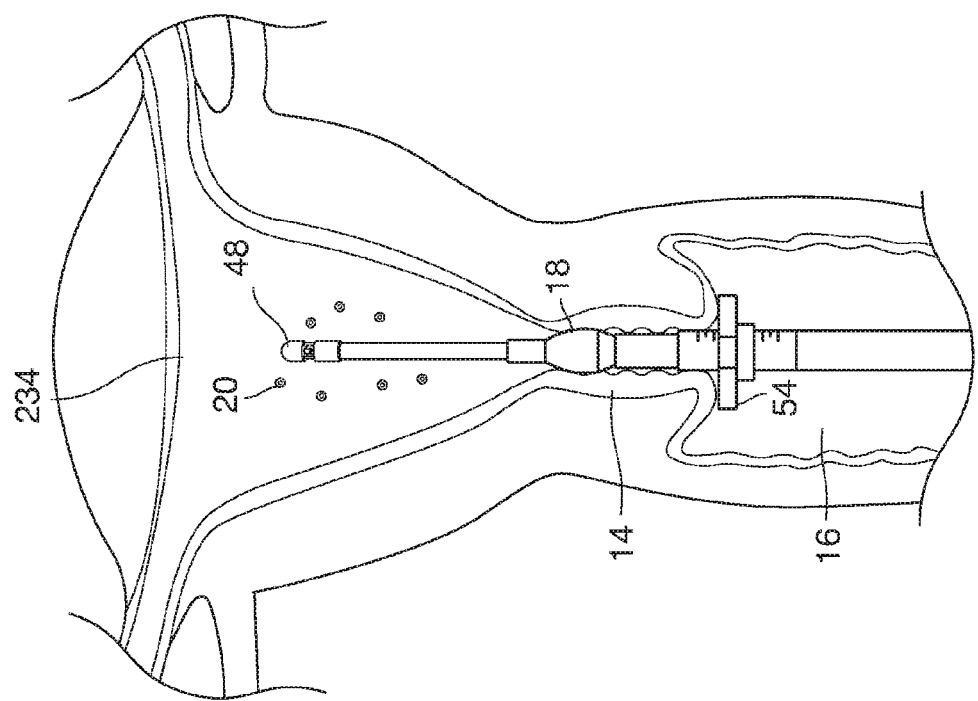

Prior to the lavage cycle, the operator primes the lavage device 10 with lavage fluid as follows: turns on the lavage device controller by pressing the 'Power' button 132 (FIG. 17) located on the control panel of the controller; presses and holds the 'Prime' button 134 on the control panel of the controller; and holds the 'Prime' button 134 down until the lavage fluid is pumped through the fluid supply line 28 and the suction recovery channel 32 of the lavage device 10 and deposits fluid into the embryo recovery trap 34. After priming is complete, the operator removes the priming cap 350 and the device is ready for insertion into the patient. The lavage procedure is conducted as follows:

i) Intracervical Insertion: The procedure begins with insertion of the lavage device 10 into the uterine cavity 12 via the cervical canal 14 through the vagina 16. The lavage device 10 is inserted until the cervical stop 54 rests against the external surface of the cervix 14 (external cervical os 232) creating a fluid-tight seal, protecting the vagina 16 (FIG. 19). The deflated balloon collar 18 lies at the end of the cervical canal 14 at the entrance to the uterus (internal cervical os 230).

ii) Insufflation: Creation of Cervical Seal: The cervical seal balloon collar 18 is then inflated (FIG. 1) to provide a watertight seal at the internal cervical os 230 to prevent the loss of lavage fluid around the lavage device 10. This is done by depressing the syringe 56 until 1.5 cc to 3 cc of fluid, air or liquid, is injected into the balloon collar 18, or until sufficient resistance to balloon inflation is felt by the operator. The stopcock 60 is then closed to ensure the balloon collar 18 remains inflated throughout the duration of the procedure. In some cases, especially for nulliparous women, balloon inflation may not be required to gain a seal at the internal cervical os 230.

iii) Positioning of Catheter Tip in Center of Uterus: The final step prior to performing the lavage cycle is positioning of the atraumatic tip 48 as close to the center of the uterine cavity 12 as possible. The operator utilizes predetermined dimension information that specifies the length of the uterus from the external cervical os 232 to the fundus 234 to set the position of the catheter tip 48 as follows: hold the lavage device using the handle 50; extend the atraumatic tip 48 into the uterine cavity 12 (FIG. 20) by pushing the manifold 42 slowly forward until the tip 48 touches the fundus 234. The operator knows when the catheter tip touches the fundus when resistance is felt as the tip 48 is being extended into the uterus while depressing the manifold 42. The operator retracts the atraumatic tip 48 2.0 cm back from the fundus 234 (FIG. 21). The operator may opt to utilize uterine ultrasound either abdominally or vaginally to verify correct placement of the atraumatic tip 48. The lavage device 10 including its fluid supply and vacuum lines is now in its semi-extended position, approximating the center of the uterus where blastocysts 20 are located. The operator may extend the device position as the lavage cycle progresses as needed or desired for use.

Figure 22:
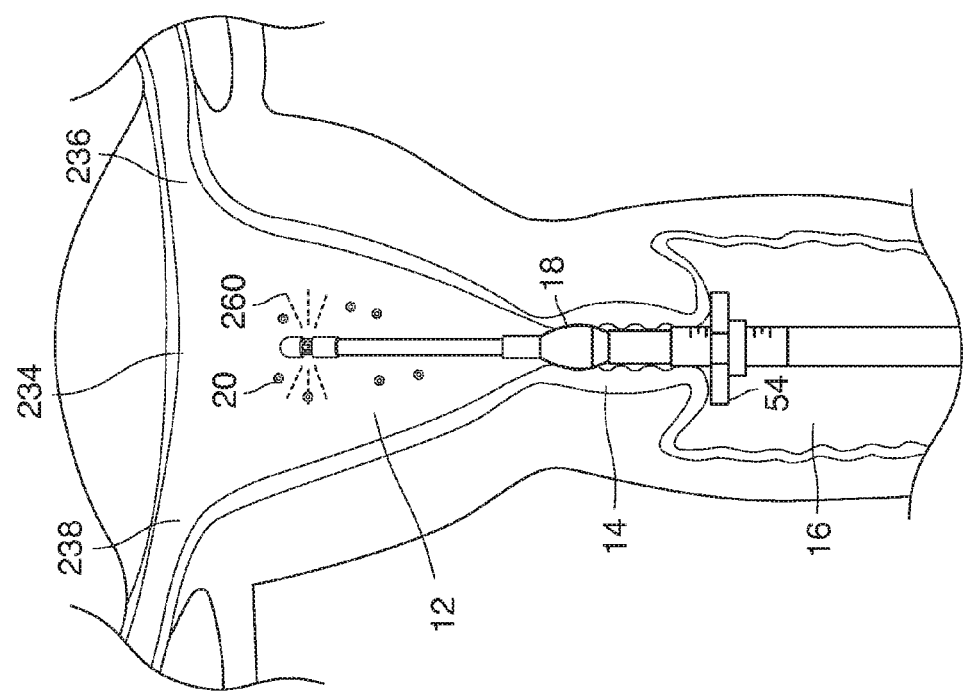
Figure 23:
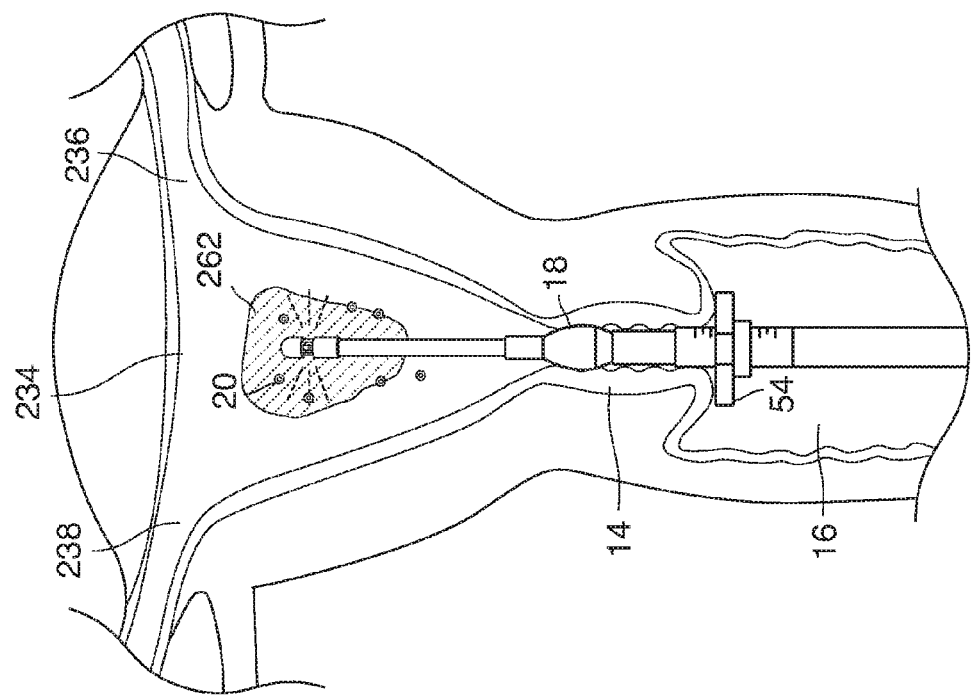
Figure 24:
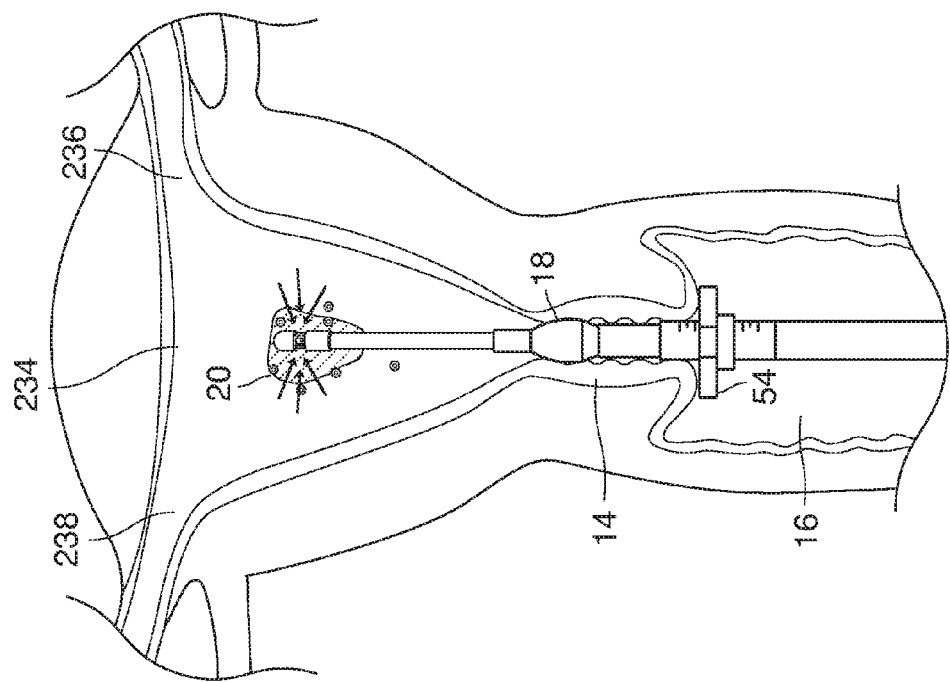
Figure 25:
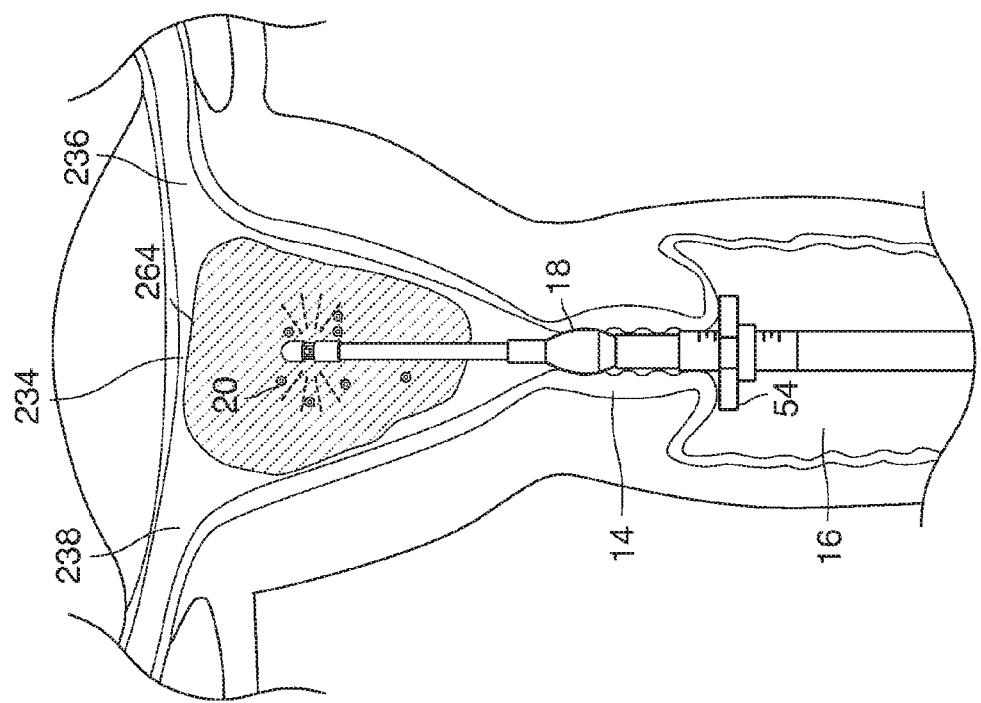
Figure 26:
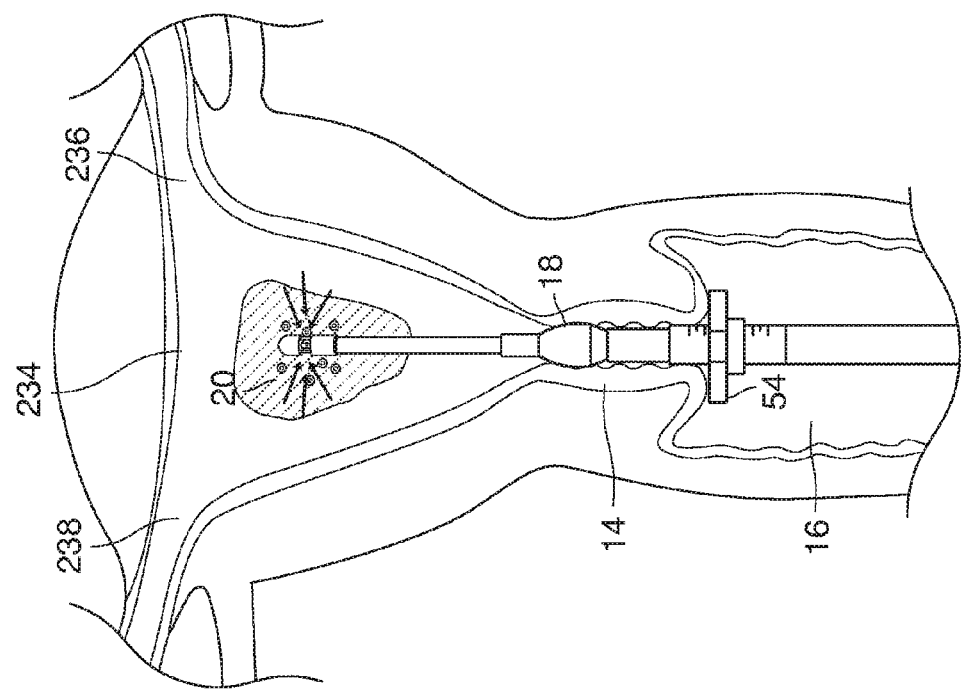
Figure 27:
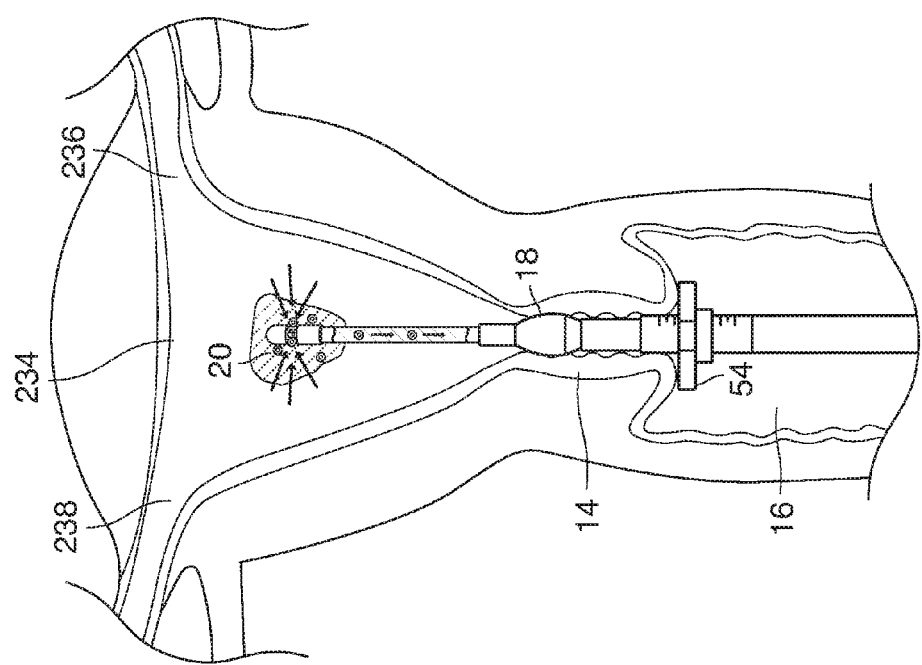

Alternatively, the position of the atraumatic tip 48 is determined by monitoring the indicia 82 on the stabilizing bar 44.

iv) Uterine Lavage & Embryo Recovery: The lavage cycle (FIGS. 22-27) is started by depressing the 'treat' button on the control panel. The first stage of the lavage cycle is begun by injecting a small amount of fluid 260 (FIG. 22) into the uterine cavity 12 for form a puddle 262 of fluid (FIG. 23) encompassing the blastocysts 20. All of the fluid present in the uterine cavity 12 is then suctioned into the catheter (FIG. 24) along with one or more entrained blastocysts 20. The second stage of the lavage cycle is begun by injecting a larger amount of fluid into the uterus to form a larger puddle 264 (FIG. 25). All of the fluid present in the uterine cavity 12 is then suctioned into the catheter (FIGS. 26 and 27) along with one or more entrained blastocysts 20.

Lavage fluid is delivered and vacuumed in alternating pulsed cycles of inject, dwell, and vacuum through the dual lumen atraumatic tip 48. Using the indicia 82 on the stabilizing bar 44, the position of the atraumatic tip 48 can be changed for each cycle. For example, a first cycle can be with the atraumatic tip 48 at zero extension, and cycles two through five can be at increasing extension increments that are a quarter of the distance to the fundus 234, with the amount of fluid delivered increasing in each subsequent cycle. The dual focused streams of fluid directed to the uterine cavity wall at a point below the internal ostia 236, 238 form a functional hydraulic wall through which the embryos cannot move retrograde from the middle uterine cavity into the respective right and left internal tubal ostia 236, 238.

Figure 28:
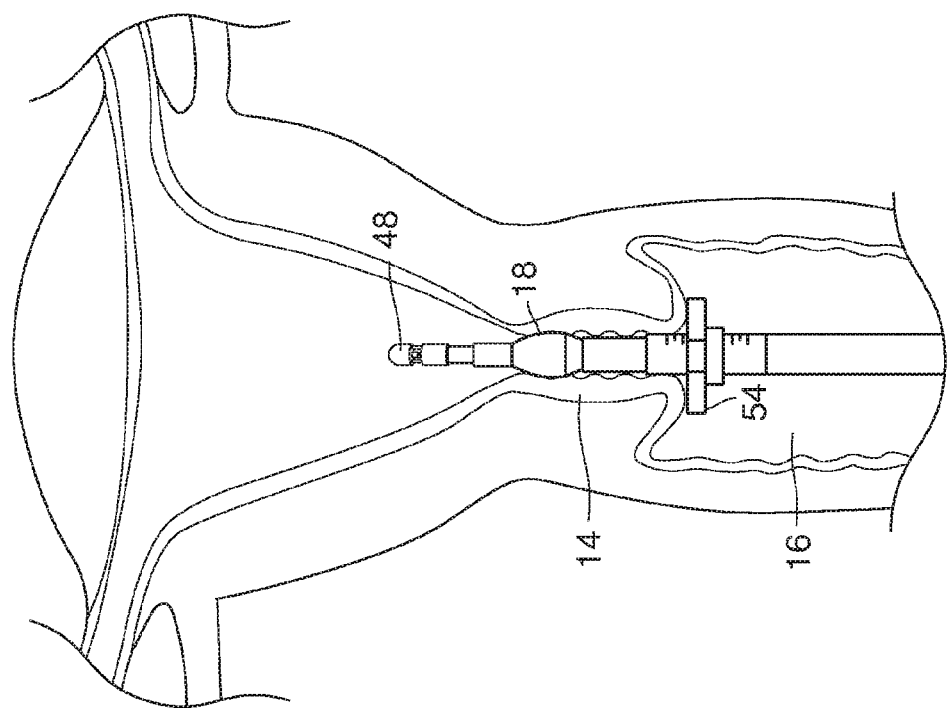
Figure 29:
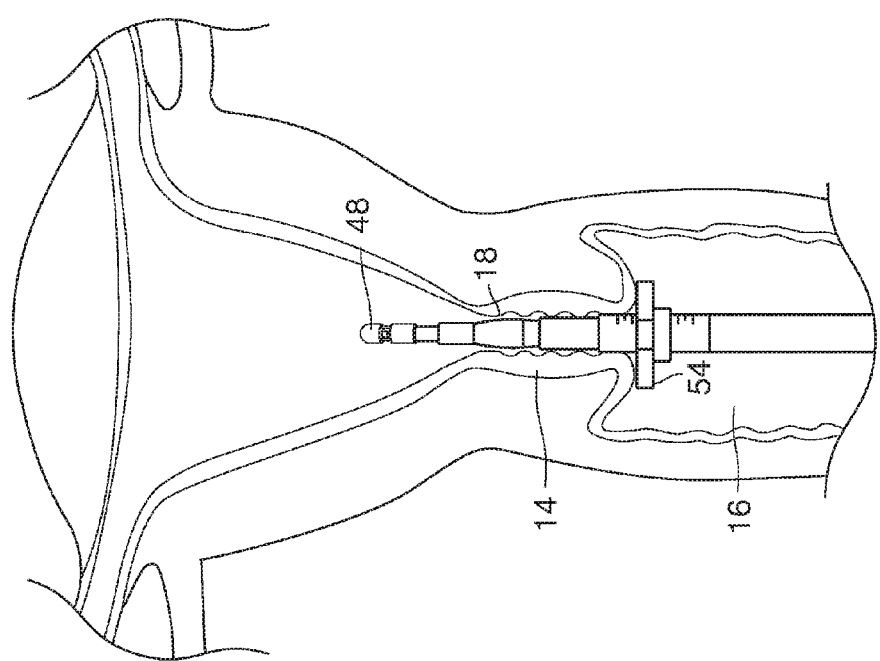

The lavage cycle is repeated and controlled by the lavage device controller. The lavage cycle operates for approximately 3 minutes, or until 100% of the lavage fluid (maximum 5 minutes) located in the fluid bag 30 is cycled through the lavage device 10, into the uterus and removed via the suction recovery channel 32 into the embryo recovery trap 34. The operator monitors the lavage cycle visually by watching fluid flow. While the lavage cycle is operating the fluid flow will pulse through the fluid supply line 28 and suction recovery channel 32. The fluid quantity will decrease in the fluid bag 30 and increase in the embryo recovery trap 34. The recovered lavage fluid will appear cloudy due to presence of uterine fluid and endometrial tissue captured from the lavage process and recovered from the uterus. The embryos are withdrawn from the uterus with an efficiency of at least 80%. The embryos are withdrawn from the uterus with an efficiency of at least 90%. The embryos are withdrawn from the uterus with an efficiency of at least 95%. Desynchronization of the endometrium is caused to reduce the chance that any embryos remaining in the uterus will form a viable pregnancy.

v) Jamming: (optional step to address lack of fluid flow in catheter during the lavage cycle): Jamming is the term which describes a lack of fluid flow and can occur due to the buildup of endometrial tissue at the atraumatic tip 48. The following steps can be taken in the event of jamming: press the Pause button on the lavage device controller control panel, adjust the position of the catheter tip and restart the lavage cycle, repeat as needed, when flow is detected in the suction recovery channel allow the lavage cycle to complete.

vi) Completion and Stop of the Lavage Cycle: The lavage cycle is complete when (1) the fluid bag is empty and (2) the controller system has operated for at least one minute after all fluid is visibly removed from the fluid bag, supply line and suction recovery channel. The lavage procedure automatically ends after a sustained duration of vacuum only cycle is completed or when the operator depresses the 'Finish' button twice. The operator then turns off the lavage controller by depressing the power button.

vii) Removal of Lavage device: The operator removes the lavage device as follows: pull the manifold 42 away from the handle 50 to retract the inner catheter 40 into the outer guide member 38 (FIG. 28); deflate the balloon collar 18 by opening the stopcock 60 and retracting the syringe 56 to 0 cc (FIG. 29); the lavage device 10 is then slowly removed from the cervix 14.

Figure 30:
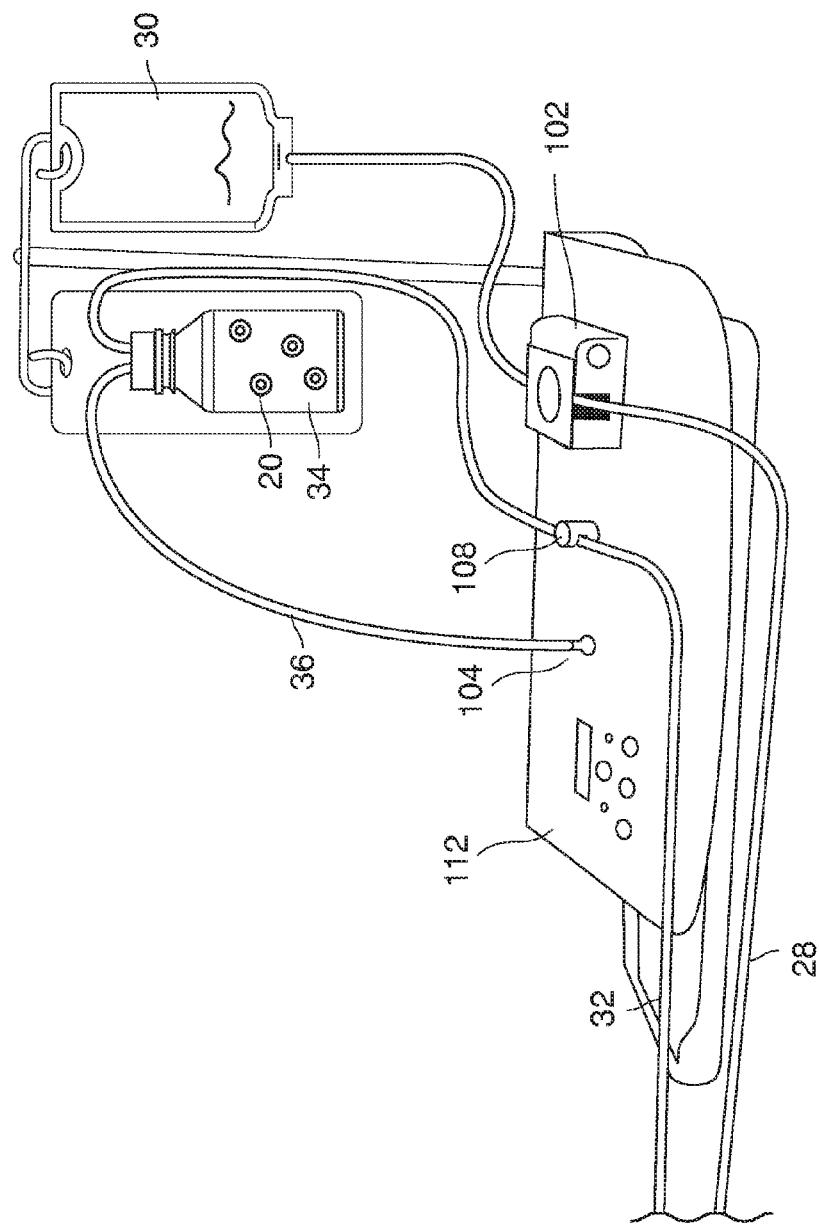
FIG. 30 is a close-up partial view of the control cart of FIG. 15.
Figure 31:
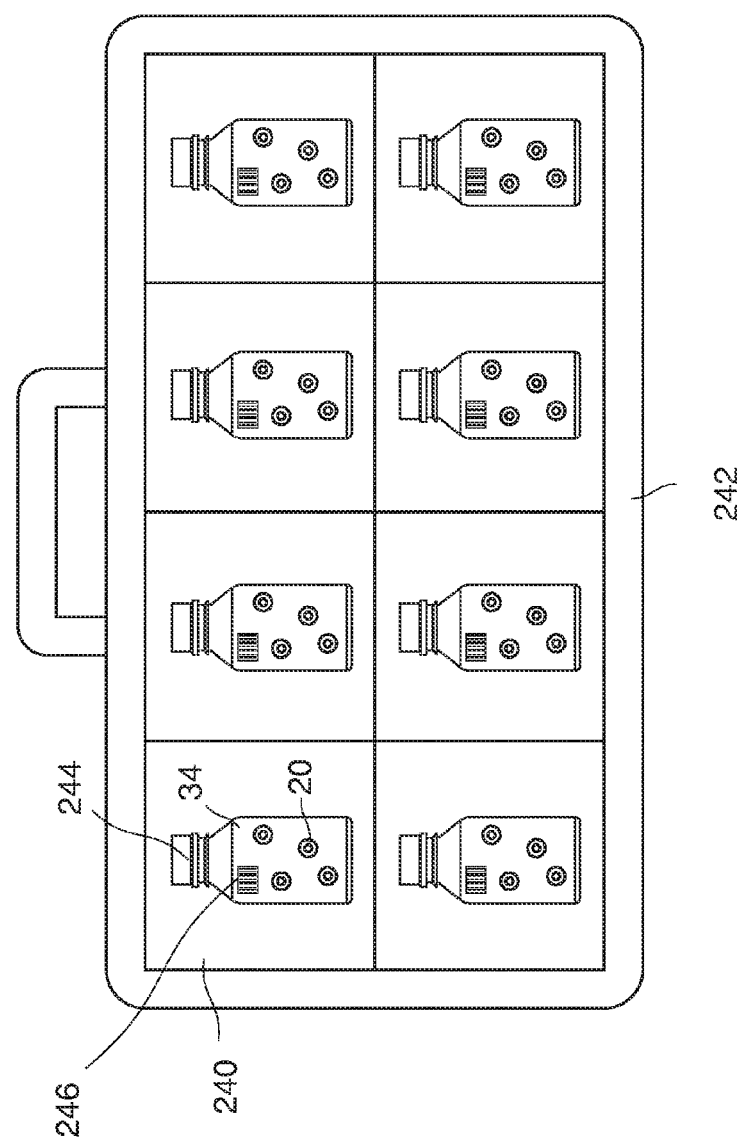
FIG. 31 illustrates a step of a lavage procedure.

Referring to FIG. 30, the recovered blastocysts 20 are located in the embryo recovery trap 34, which is also the container used for transportation of the blastocysts 20 to an embryology laboratory. The operator disconnects the embryo recovery trap 34 from the device 10 by 'snapping' the connections just above the top of the embryo recovery trap 34. The embryo recovery trap 34 is then placed into a preheated container 240 (FIG. 31) that secures the embryos for transport, ensuring that the recovered blastocysts 20 are in an environment in which they will thrive. Multiple individual sample containers 240 can be placed in a transport carrying case 242 (FIG. 31). Each recovery trap 34 is sealed by a glass stopper 244 and labeled with an ID label 246.

The fluid used in the lavage cycle may be lactated Ringers, HTF (Human Tubal Fluid), modified HTF, or HEPES-buffered media. The operator determines appropriate solutions based upon knowledge and preference. The operator receives recommendations as follows for fluid choice: (1) non-heparin based media (2) non CO2 based media that is approved/generally accepted for use in humans.

The uterine lavage procedure is performed under low flow and vacuum conditions, not to exceed the maximum pressure allowed by the device of between 2 ounces per square inch and 20 pounds of pressure per square inch and 10-14 Hg of vacuum pressure to maintain the integrity of the blastocysts during fluid delivery and removal. The uterine cavity is not expanded or pressurized. The lavage device 10 does not include any members that act to expand the uterine cavity, as such an expansion can introduce air into the uterine cavity, which can kill the blastocysts 20. The lavage process, as well as its preparatory steps and finish instructions, are designed to prevent the introduction of air into the uterine cavity to ensure the health and integrity of the recovered blastocysts.

Figure 32:
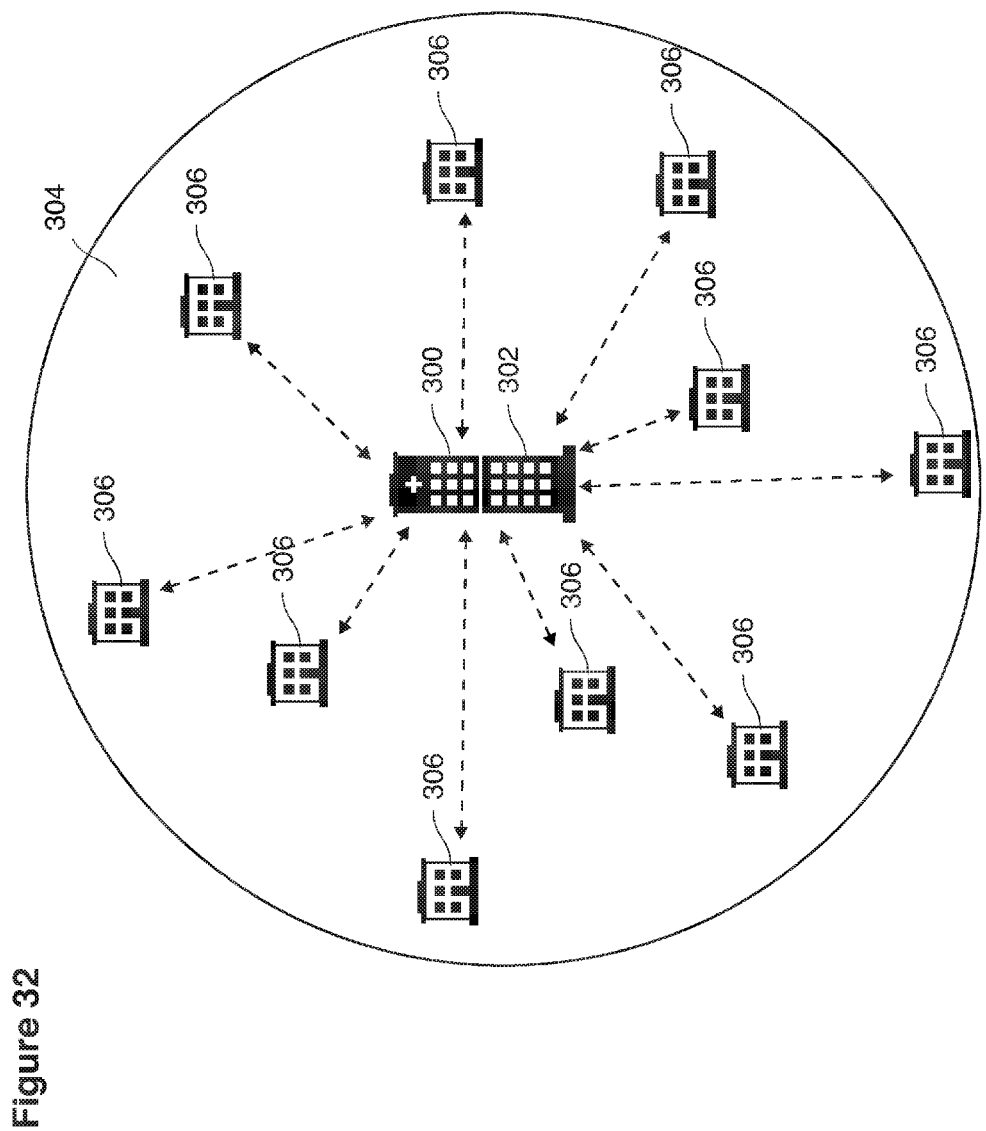
FIGS. 32-35 illustrate aspects of business models.
Figure 33:
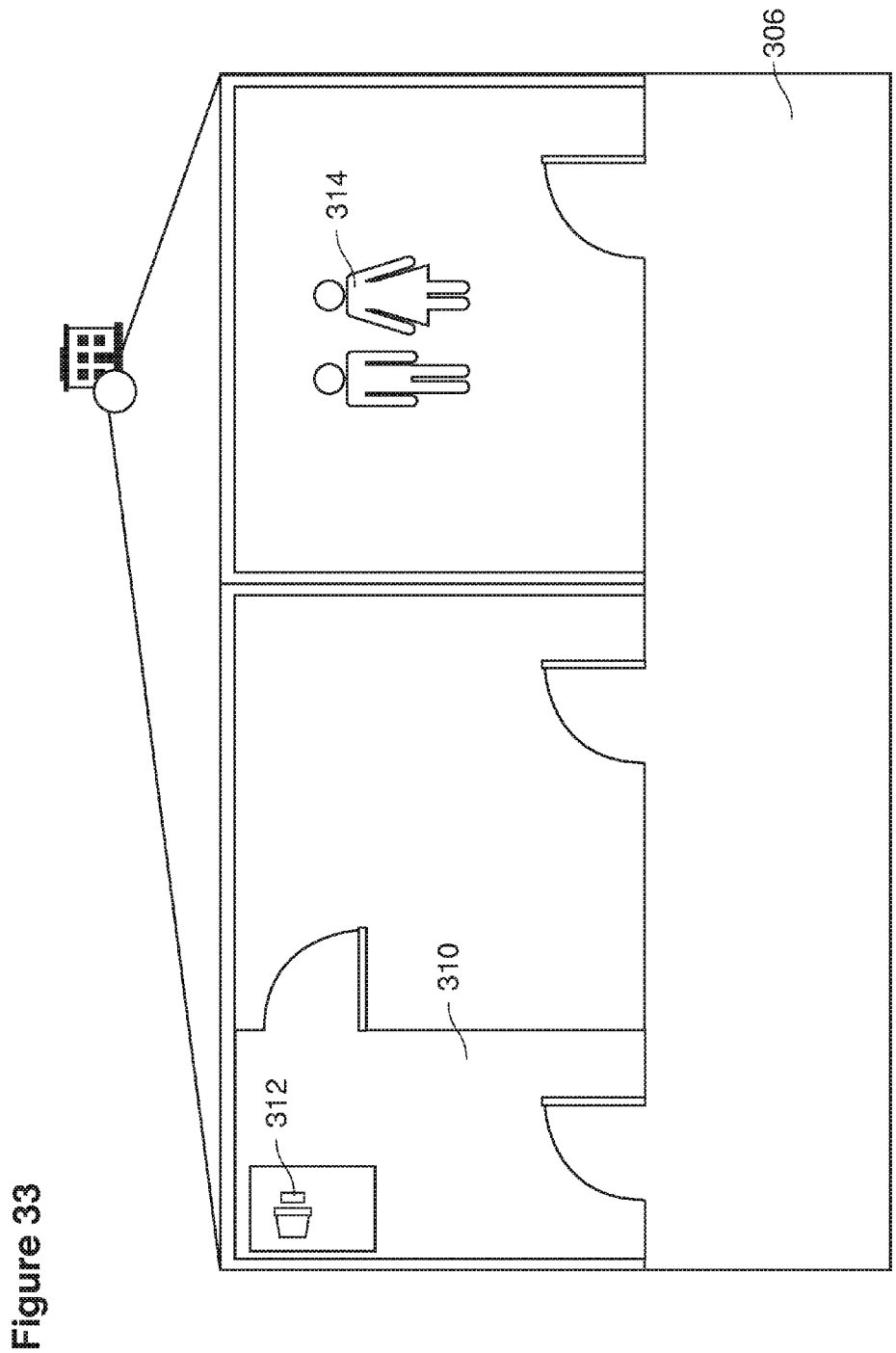
Figure 34:
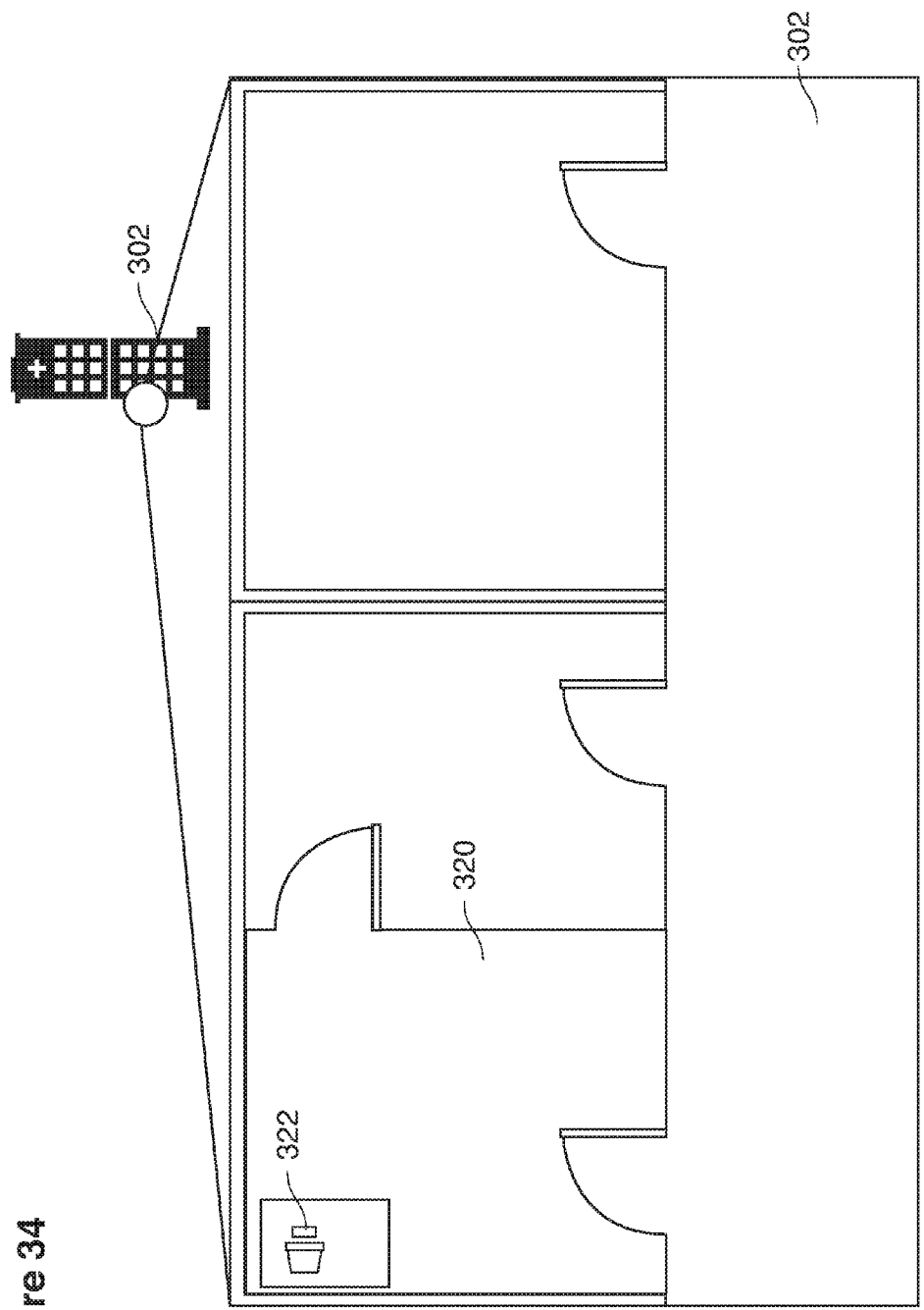
Figure 35:
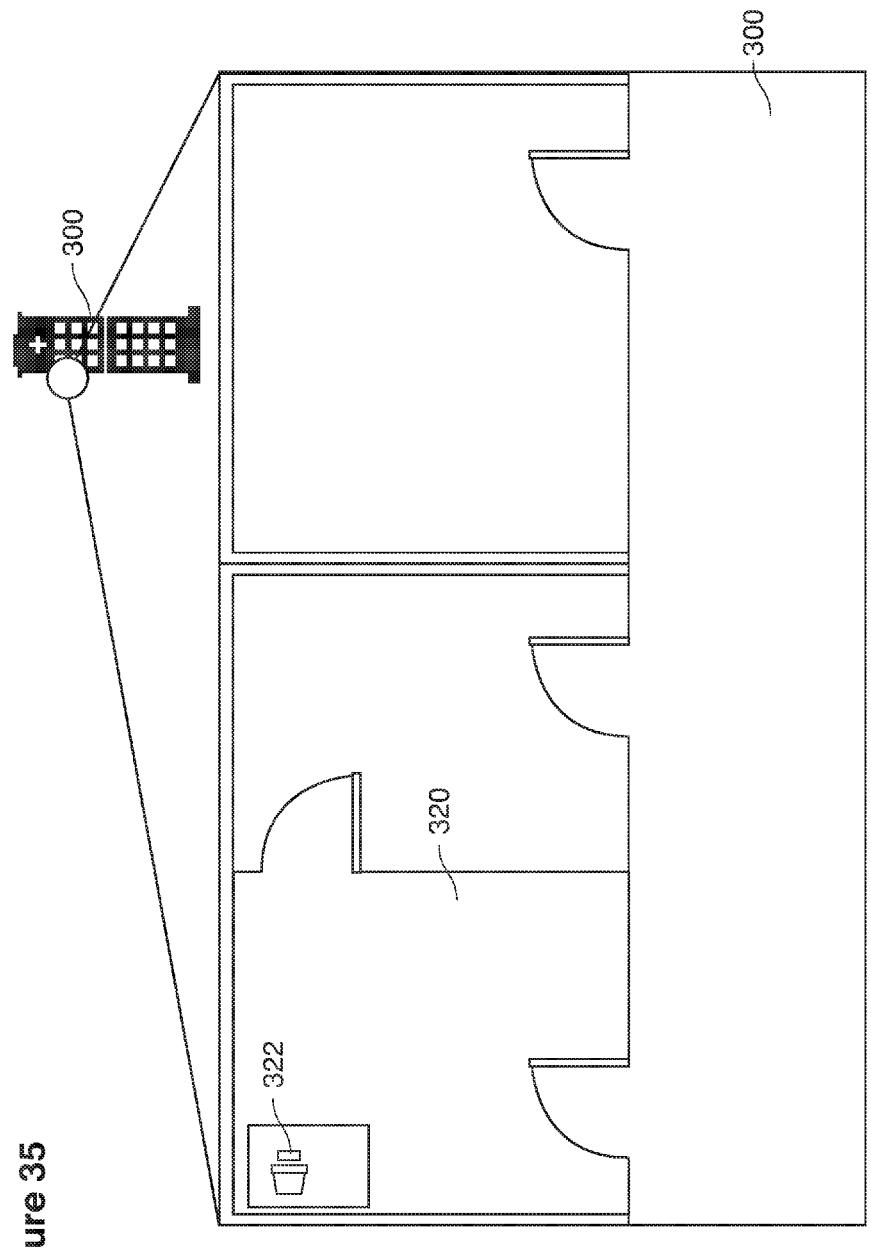

Shown in FIG. 32 are examples of how the procedures can be delivered and managed. A corporate managed regional coordination center 300 (also sometimes called the host of the network) owns and manages or franchises the operation of a number of core laboratories 302 (only one shown) located in high-density population centers across the United States. The location of each of these laboratories 302 is based upon a service area 304 that is within a defined surface travel time or distance to the laboratory 302. For example, a service area can be one served by ground transportation of a distance of approximately 150 miles radius or less than 4 hours transportation time from the laboratory 302, or with reliable delivery by air to the laboratory 302 within a flight time of less than 4 hours. Examples of suitable cities include New York (2 centers), San Francisco, Los Angeles, Boston, Chicago, Philadelphia, Washington D.C., Seattle, Minneapolis, Miami, Atlanta, Denver, Dallas, Phoenix, and Memphis.

In some implementations, each of the core laboratories 302 is imbedded in an existing embryological molecular genetic service laboratory already existing in a major, high profile medical center. Each of the core laboratories 302 is supported and electronically linked to its own regional network of subscriber clinics 306. The host 300 of the network leases or partners with existing core laboratories 302 capable of providing embryology, cryogenic, and molecular genetic services (or some part of them) for embryos acquired in their service areas same day.

The network host's subscriber clinics 306 are points of patient contact and care services. Physicians and support staff working in these local clinics 306 are subscribers to the network host's systems. Among other things, to become a subscriber a clinic has to include high security areas 310 in their clinics and computer linkages 312 that are managed by the network host 300 and solely devoted to network host operations at their site. Physicians and support staff working in subscriber clinics 306 will have been previously established as practitioners of reproductive endocrinology, infertility, and genetics.

Patients 314 seeking the network host's services are referred to a subscriber clinic 306 located near their home or business. There need be only limited disruption of a patient's personal life while she is receiving services in the system. The ordering of the central host's embryological services, genetic testing, and obtaining of results is as simple as ordering routine laboratory testing as practiced today.

As seen and experienced by an individual patient 314, the process begins with the patient 314 entry at a local network subscriber clinic 306, embryo recovery at the clinic, followed by embryo diagnosis, decision, treatment if possible, and replacement of her embryos at the subscriber clinic 306. The steps of counseling, consenting, superovulation, artificial insemination, and lavage take place in subscriber clinics 306 under the direction of the clinic physician and staff. Network personnel perform lavage at the subscriber clinic 306, transport the recovered blastocysts, process the blastocysts at the core laboratory 302, return the blastocysts to the subscriber clinic, and transfer the blastocysts back to the women's uterus at the subscriber clinic 306, with follow-up and confirmation of the pregnancy being done in the woman's local health care system.

Patient 314 entry begins at the subscriber clinic 306 where she and her partner have been referred by herself or by a physician in anticipation of her becoming pregnant. After review of the genetic reproductive history, a subscriber's reproductive endocrinologist geneticist will make the decision that the network's procedure is appropriate and will contact the network's core laboratory 302 through their subscriber link. The patient's data will be entered locally at the subscriber clinic 306 along with appropriate demographics, financial, and insurance data. The network regional coordinating center 300 will review the data entries and, as appropriate, approve of that patient's entry after review of history and laboratory data.

The network's nurse practitioner staff will see the patient in person at the subscriber clinic 306, customize and fit the lavage device to the specific anatomy of that patient using traditional or 3D ultrasound imaging, and approve her for launch (starting superovulatory drugs) of her cycle. The network's regional coordinating center 300 will then authorize initiation of the drug induced superovulation induction. Subscriber clinic physicians prescribe and administer superovulatory drugs under protocol, conduct the monitoring, and report the patient's progress in real time using online links to the network's regional coordinating center 300. Superovulation (actual release of oocytes for fertilization) will be triggered by protocol and managed by subscriber clinic physicians. The woman will then appear in the subscriber clinic 306 with her partner, and after documenting security clearance using electronic chips and face-iris recognition (in other words, confirming that the woman is the person who she purports to be and is the patient to be processed), the subscriber clinic personnel, with approval by the network regional coordinating center 300, will perform intrauterine insemination of the woman at approximately 36 hours after triggered superovulation. Sperm samples will be prepared in the onsite network secure laboratory site 310 with identities re-confirmed electronically by the patient's and her partner's electronic identification cards that are programmed, for example, with confirmatory facial recognitions and iris scans.

Uterine lavage will be performed at the subscriber clinic by the network nurse practitioner at between 5 and 7 days after insemination. The recovery fluid is diluted with embryo protective transport media added immediately to the lavage fluid at recovery and is transported in sealed insulated containers 240 (FIG. 31) that are marked by the electronic identification chips 246 linked to the women and her partner.

After lavage, the subscriber clinic 306 electronically notifies the core laboratory 302 by way of the secure computer network link of the status and location of all blastocysts 20 in process in the network at that time. At each step in the process after lavage, information recorded electronically as identity chips attached to each clinical and laboratory step is scanned and stored in the network system data processing facilities to maintain a history of the steps and the current location of the blastocysts 20. Thus, the exact location of all blastocysts and cells retrieved from all patients is known in real time as identification chips are passed through scanners from lavage, to recovery in the laboratory, to biopsy, to genetic diagnosis, genetic therapy, or sex determination (or any two or more of those), to freezing, thawing, and placement back into the patient. The identity of all patients and their partners is confirmed, for example, by iris/retina scans, electronic face recognition, and identification cards at each contact. Software is also be used to manage lab reports, clinical data from each patient and her partner, contact information, and billing and insurance arrangements.

Blastocysts 20 are delivered to the core laboratory 302 in the same lavage fluid, diluted in transport media that was used for the lavage recovery. The containers 34 in their insulated transport blocks 240 obtained from the day's procedures are carried in secure carrying cases 242 transported by the nurse practitioner. On arrival at the core laboratory 302 and on delivery to a secure network laboratory space 310 (FIG. 54), the lavage containers 34 are matched electronically after scanning to the identification system and then placed in an individual space allocated only to those blastocysts. An identification database 322 maintained in the corporate regional coordinating center 302 contains all instructions on the type of biopsy procedure to be performed, and the diagnostic tests to be performed on the biopsied cells relevant to that patient.

After the embryologist manually isolates and confirms identify from scan of the electronic chip 246 attached the transport container 34, each of the blastocysts is graded for viability by the embryologist, placed on a micromanipulator in an electronically marked petri dish, and undergoes selective trophectoderm-inner cell mass biopsy. Approximately 10 to 20 trophectoderm 334 or inner cell mass cells 336 are obtained and submitted to molecular genetic analysis as directed by orders in the patient's database and dependent upon indications for the specific procedure.

Figure 36:
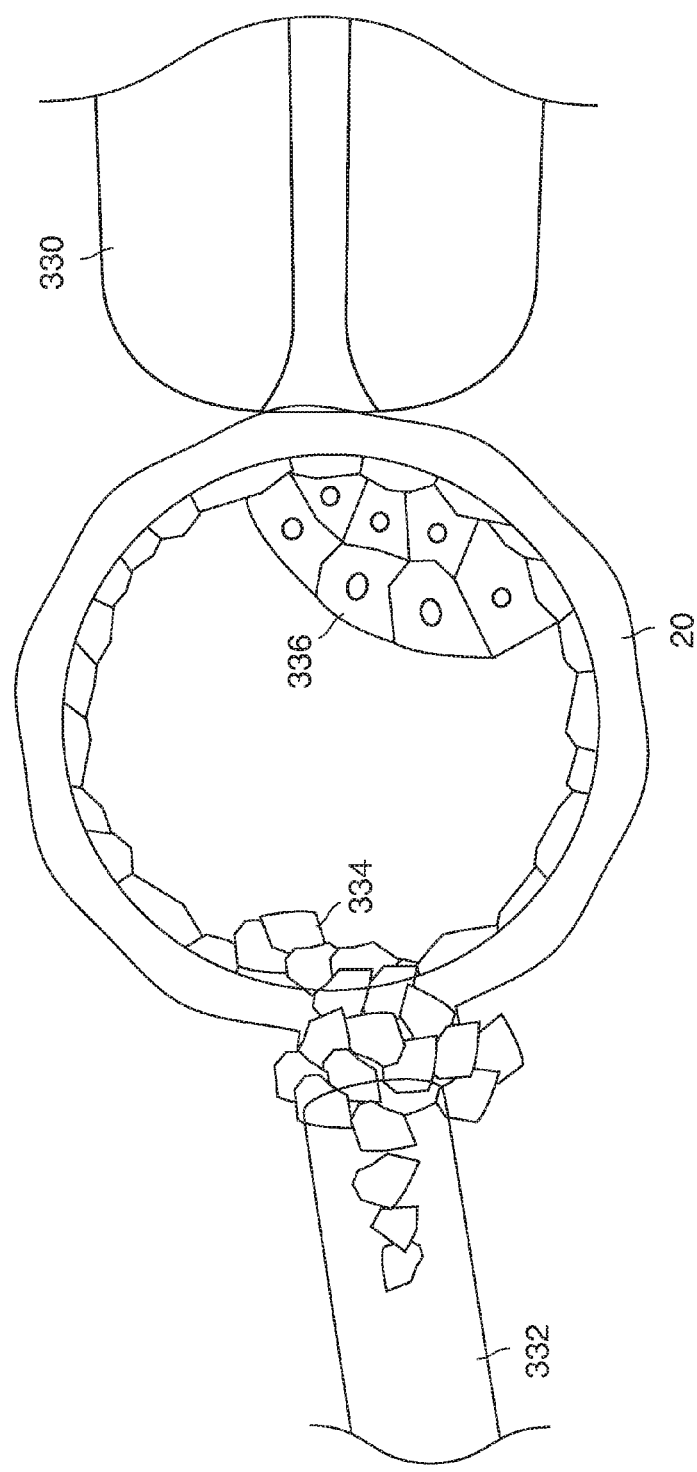
FIG. 36 illustrates a procedure performed on a blastocyst.

Referring to FIG. 36, when utilizing a micromanipulation apparatus, individual blastocysts 20 in individual Petri dishes under blastocyst culture and heated fluid (typically 37C) are positioned onto the tip of a fire-polished pipette 330 and stabilized by application of gentle suction on the lumen of the pipette. The zone pellucida is opened mechanically with another pipette 332 or with a laser beam to expose either the trophectoderm (future placenta—334) or inner cell mass (future fetus—336) of the blastocyst, which are removed via the pipette 332. It is likely that with existing or future nano surgical technology it will be possible to recover from one to many targeted cells 334, 336 for molecular genetic diagnosis or sex determination.

The recovered trophectoderm cells 336 or inner cell mass 334 obtained from targeted embryonic regions are placed in blastocyst media in petri dishes or small tubes and then undergo molecular genetic diagnosis or sex determination or both. Molecular methods are selected for the condition being evaluated. Established techniques include one or more of (or combinations of any two or more of: in situ hybridization to evaluate chromosomal structures, polymerase chain reaction directed to detect specific mutations or other defects gene organization, whole genome hybridization, microarray gene chips, exome sequencing, or analysis of the entire human genome. A geneticist evaluates the molecular analysis in combination with information about specific clinical factors of the case. A decision is then made that leads to (a) replacing the embryo in the mother, as unaffected by the disease in question, (b) recommending an intervention such as gene therapy or transplantation of donated stem cells, or (c) recommending that the embryo not be replaced and that another embryo which is unaffected be replaced at a later time.

Figure 37:
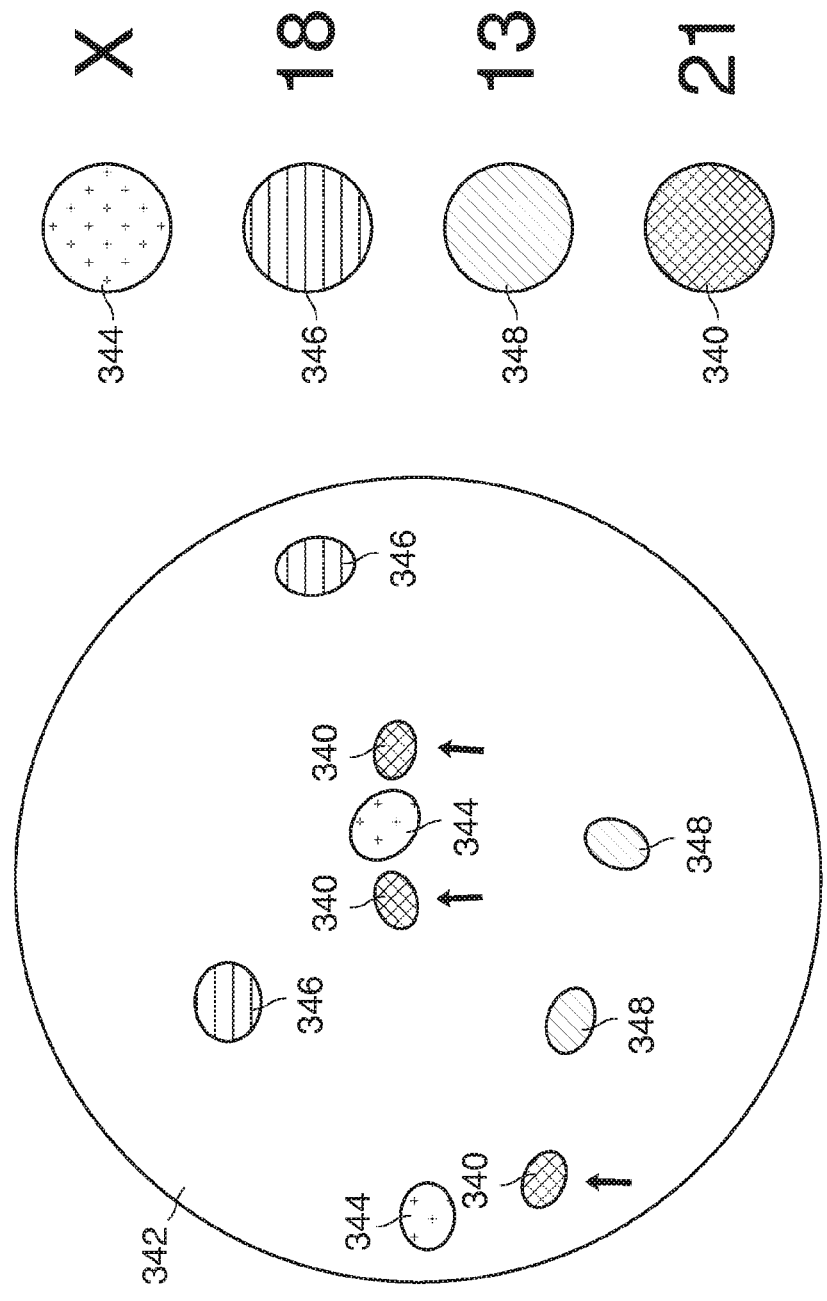
FIG. 37 illustrates a genetic diagnosis.

Referring to FIG. 37, a common example of a molecular diagnosis (Down syndrome) 340 currently possible from human blastocysts using either single trophectoderm or very early fetal cells is illustrated. This figure depicts an example in which specific areas of chromosomes are targeted at a molecular level fluorescent in situ hybridization (FISH) 342 with fluorochromes, which produce a microscopically visible signal when linked. In this example, a diagnosis of Down syndrome is demonstrated by the presence of three #21 chromosome signals 340. Also seen are two X-signals 344 indicating female gender, two (#18)-signals 346, and two (#13) signals 348 as would be encountered normally.

A wide variety of analyses can be applied. For example, the molecular analysis can include one or more of the following: in situ hybridization to evaluate chromosomal structures, polymerase chain reaction directed to detect specific mutations or other defects gene organization, whole genome hybridization, microarray gene chips, exome sequencing, or analysis of the entire human genome as indicated. Tests can be performed in duplicate for confirmation, because 10-20 cells should be adequate. The biopsied blastocysts 20 are frozen or vitrified in liquid nitrogen for preservation. Within 24 to 48 hours, the results can be placed on the secure electronic network and reported to the subscribers and discussed with the patient and partner.

The status of each embryo and the results of the genetic analysis are reported by secure link in real time to each subscriber clinic 306 through its secure computer terminal 312. The subscriber clinic 306 also contacts the patient and her partner. The subscriber selects a strategy. Blastocysts 20 identified as suitable for replacement are delivered cryopreserved to the subscriber's clinic 306 for replacement at a later time, in days, weeks or months.

At an appointed time, the frozen blastocyst 20 selected for transfer is delivered to the subscriber's clinic by the nurse practitioner in a security-coded container that is matched to the identification of the patient and her partner using an electronic identification chip. Identities of the patient and her partner are reconfirmed with facial recognition and iris/retina scans. The blastocysts 20 is thawed in the subscriber's network protected facility, photographed, loaded into a transfer catheter under the supervision of the nurse practitioner, and then transferred into the patient by the network nurse practitioner.

Resulting pregnancies are followed by the subscriber clinic and prenatal care will take place in the clinical infrastructure of the region.

Contractual arrangements between the network system and core laboratories and subscriber clinics and laboratories include secure space and equipment allocated exclusively to network operations. The glassware and all laboratory equipment involved with network is color-coded and inventoried for no other uses except network patients and personnel specially employed or contracted by the network. Every step involved in the flow and management of the blastocysts 20 is marked electronically and linked to the identity data of the patient and her partner. Births, perinatal outcomes, and genetic evaluations also take place in the local infrastructure and are documented and archived in the network database. Long-term follow-up of the births and progress of the children into adulthood is readily achievable using information from the network database with confidentiality limits set within U.S. Government standards.

The information that is derived from containers in which sets of pre-implantation embryos recovered from respective women are held is received electronically. The information uniquely identifies the sets of embryos and reliably associates them with the respective women. Digital records of the respective sets are persistently maintained that contain information about the transporting and processing of the embryos. The information is derived from secure encrypted markers associated with the containers. Each of the sets of embryos is moved from container to container in the course of transporting and processing. The digital records are maintained by a host on behalf of providers of services with respect to the sets of embryos. The host provides electronic data services to a set of clinics with respect to services provided by the clinics to women related to in vivo pre-implantation embryos recovered from the women. The providing of the data services includes collecting data that tracks the transporting and processing of the embryos, and providing access to the clinics of data that reports the tracking.

Figure 38:
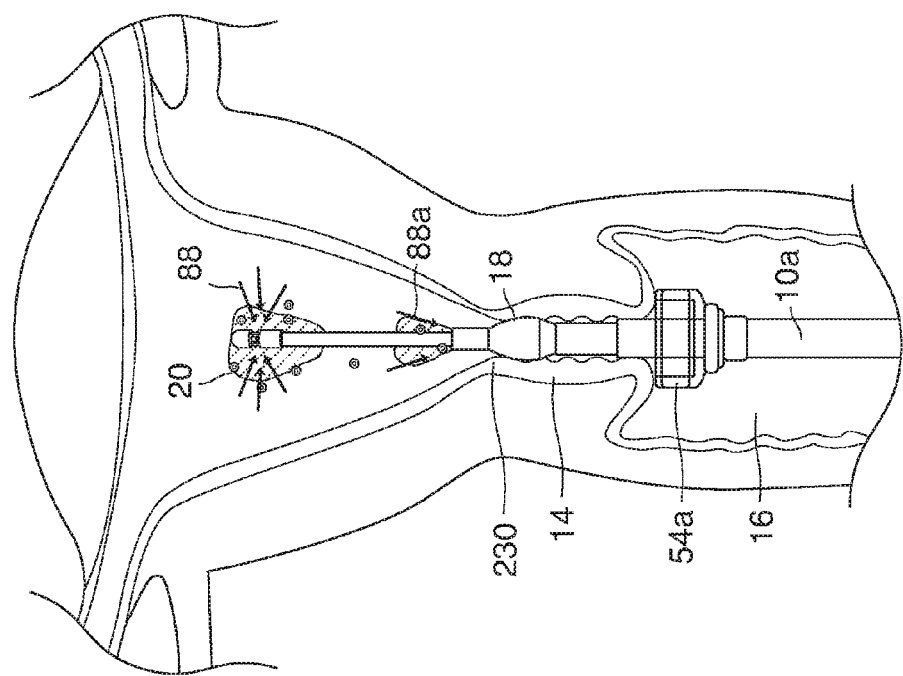
FIG. 38 is a side view of an alternative implementation of the lavage device within a female reproductive tract.

Referring to FIG. 38, a lavage device 10a can include a secondary suction port 88a provided through lumen 78 (FIG. 3A) near internal cervical os 230. The lavage device 10a includes a cervical stop in the form of a vacuum cup 54a. Vacuum applied to the cup 54a acts to attach and seal the cup 54a to the external cervical os. The operator can then pull on the lavage device 10a to straighten the woman's uterus. Any of the described lavage devices described can be used with a cervical stop 54 or a vacuum cup 54a.

Figure 39:
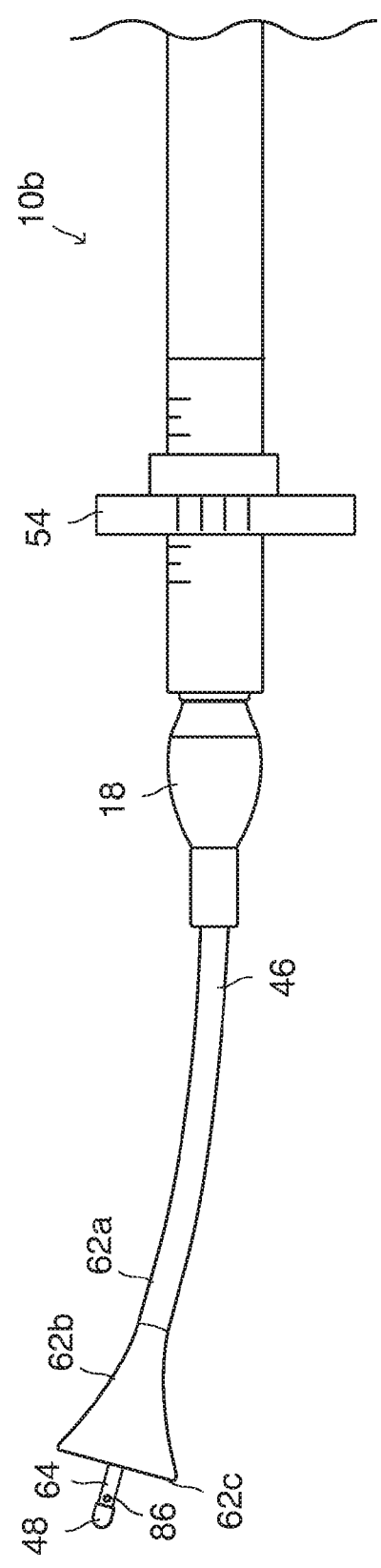
FIG. 39 is a side view of another alternative implementation of the lavage device.
Figure 40:
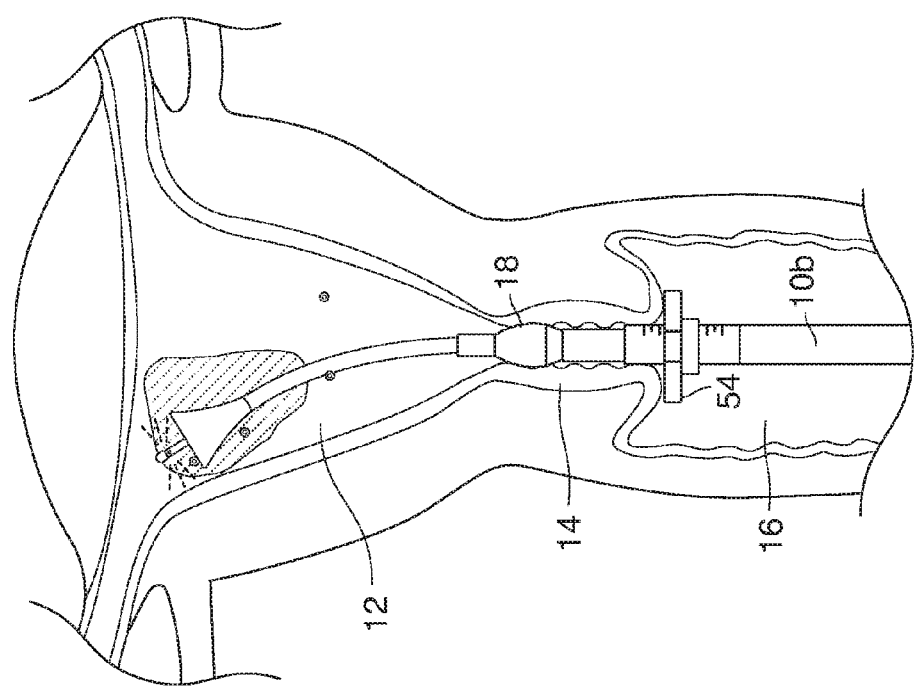
FIGS. 40 and 41 illustrate an alternative lavage process using the lavage device of FIG. 39.
Figure 41:
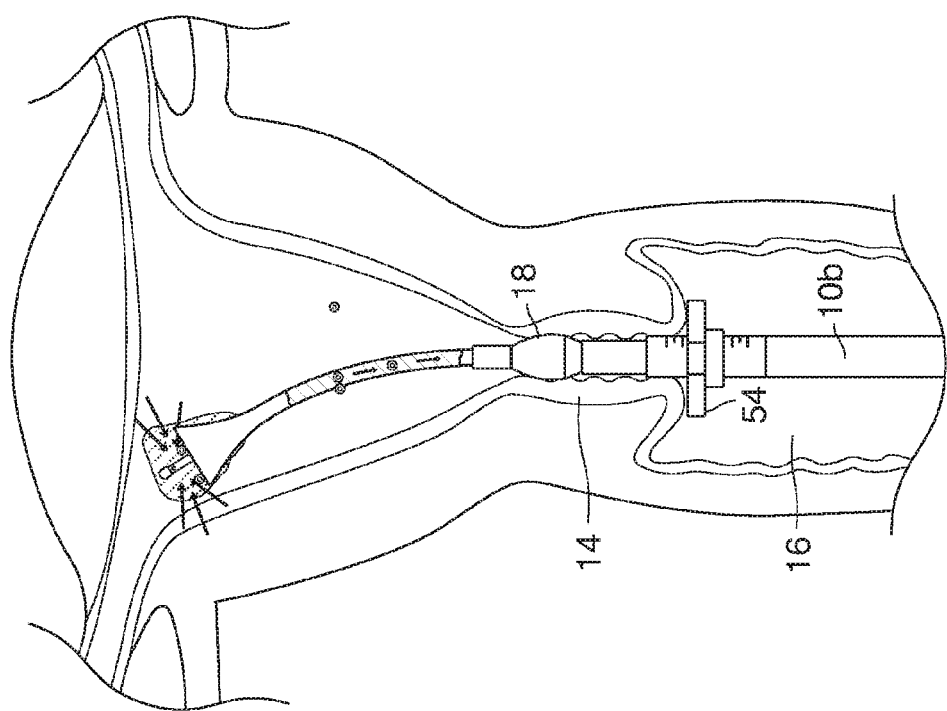
Figure 42:
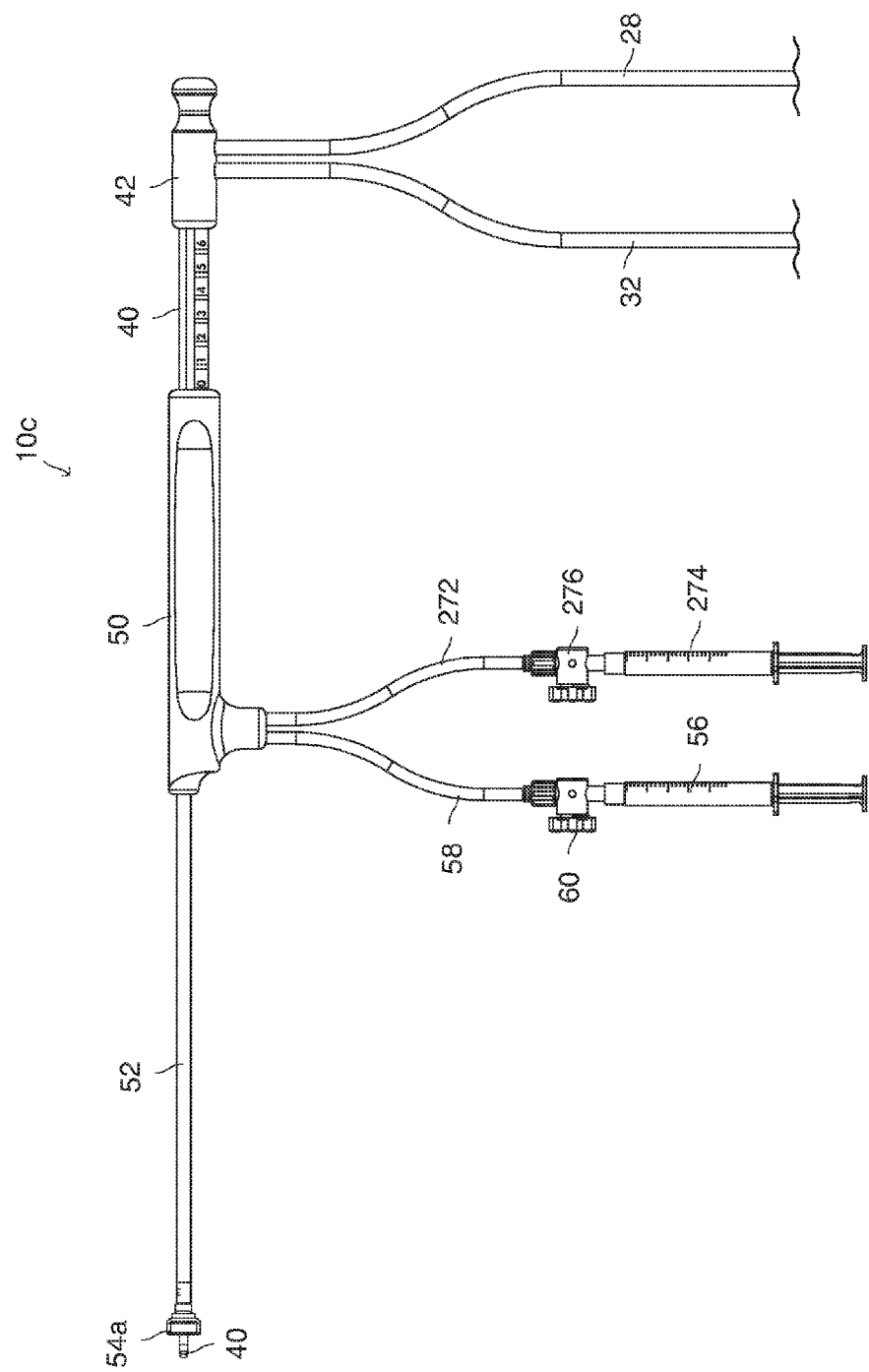
FIGS. 42 and 43 are side and close-up perspective views of another alternative implementation of the lavage device.
Figure 43:
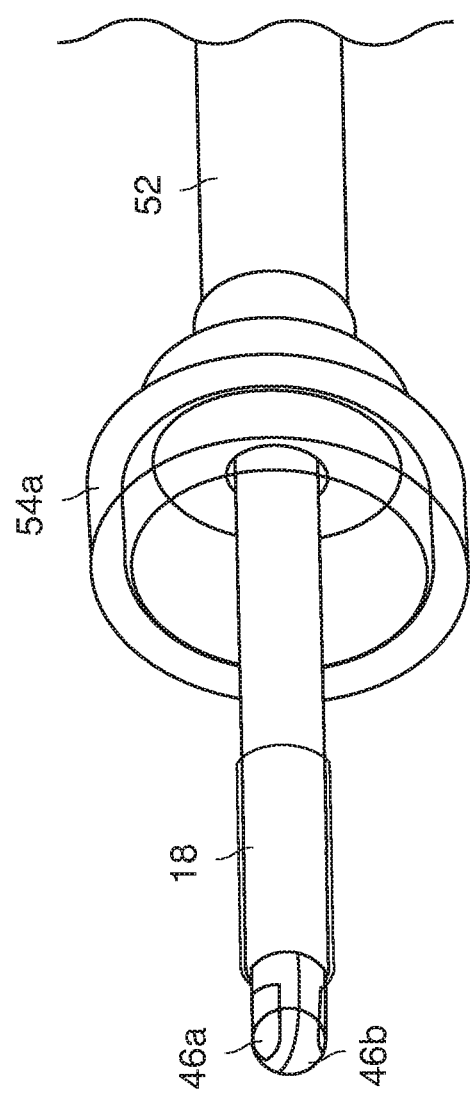
Figure 44:
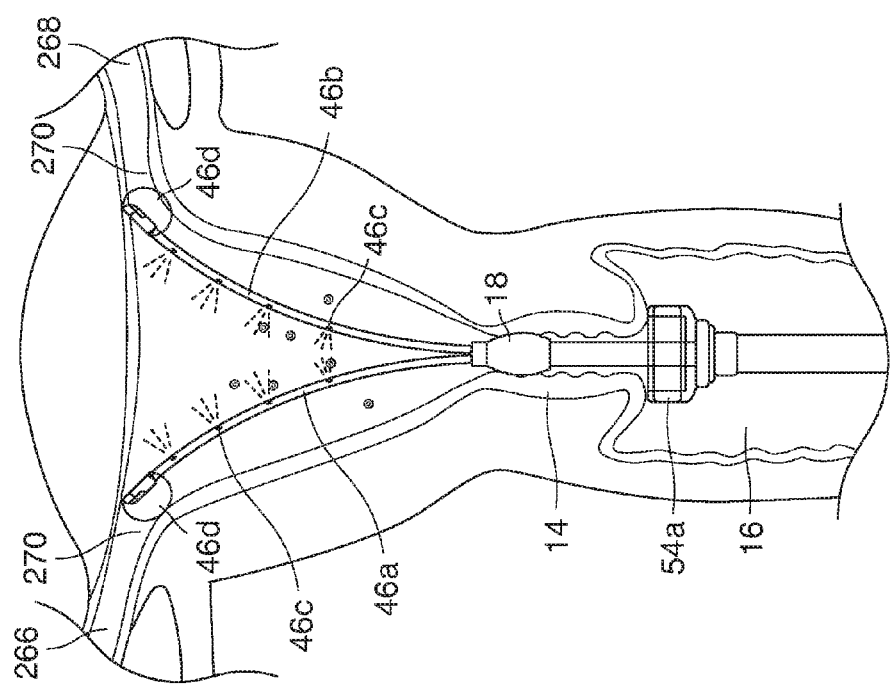
FIGS. 44 and 45 illustrate another alternative lavage process using the lavage device of FIG. 42.
Figure 45:
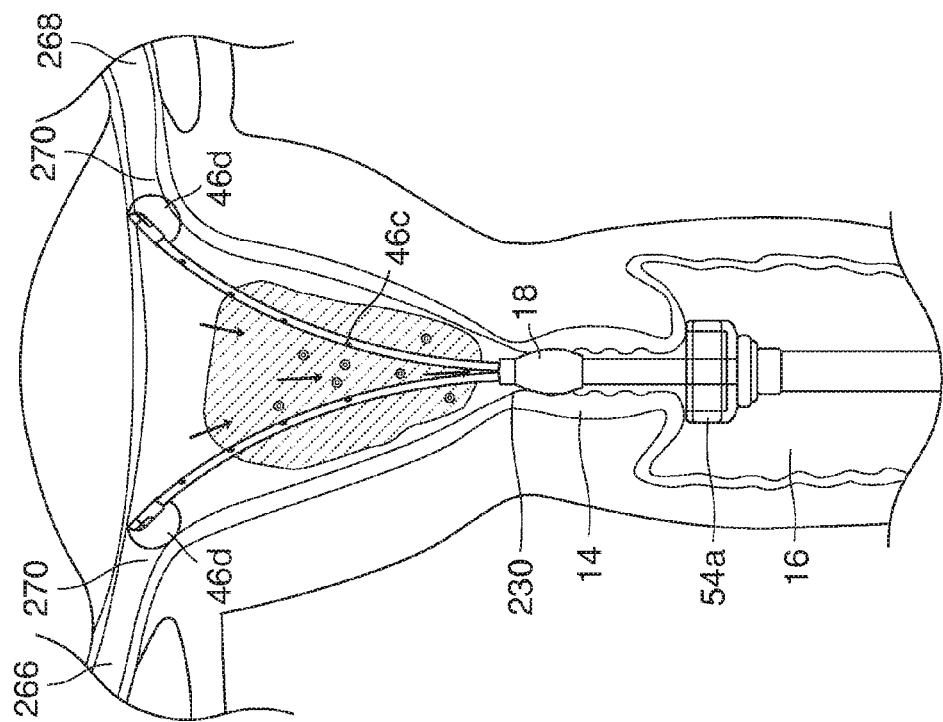

Referring to FIGS. 39-41, the outer tubular member 62a of the supply/suction line 46 of the inner catheter 40 of a lavage device 10b can terminate in a funnel 62b that flares to a large vacuum opening 62c for collecting lavage fluid and entrained blastocysts. The supply/suction line 46 can be steerable by the operator to adjust the position of the tip 48 within the uterine cavity. By positioning the tip 48 at the surface of the wall of the uterus, the lavage device uses mechanical agitation, touching and agitating the surface, to loosen mucus and recover blastocysts in the mucus. The tip 48 and funnel 62b can be moved along the wall of the uterus by rotating the lavage device 10 or extending and retracting the inner catheter 40.

Referring to FIG. 42-45, a lavage device 10c includes an inner catheter 40 have dual supply lines 46a, 46b. Each supply line 46a, 46b defines fluid openings 46c, for example, four to five openings each, for introduction of lavage fluid into the uterine cavity. The openings 46c are oriented to direct the spray of lavage fluid away from the fallopian tubes 266, 268. Each supply line 46a, 46b terminates in an inflatable cornua balloon 46d for blocking the fallopian tube ostium 270 to limit or prevent leakage of fluid into the fallopian tubes. The supply lines 46a, 46b are biased, for example, by a nitinol wire, to expand outward when advanced. Connected to the handle 50 is an inflation supply line 272, syringe 274, and stopcock 276 for inflating and deflating the balloons 46d. Fluid aspiration (FIG. 45) occurs near the internal cervical os 230 and can be through a lumen located between supply lines 46a, 46b or through lumen 78 (FIG. 3A).

Figure 46:
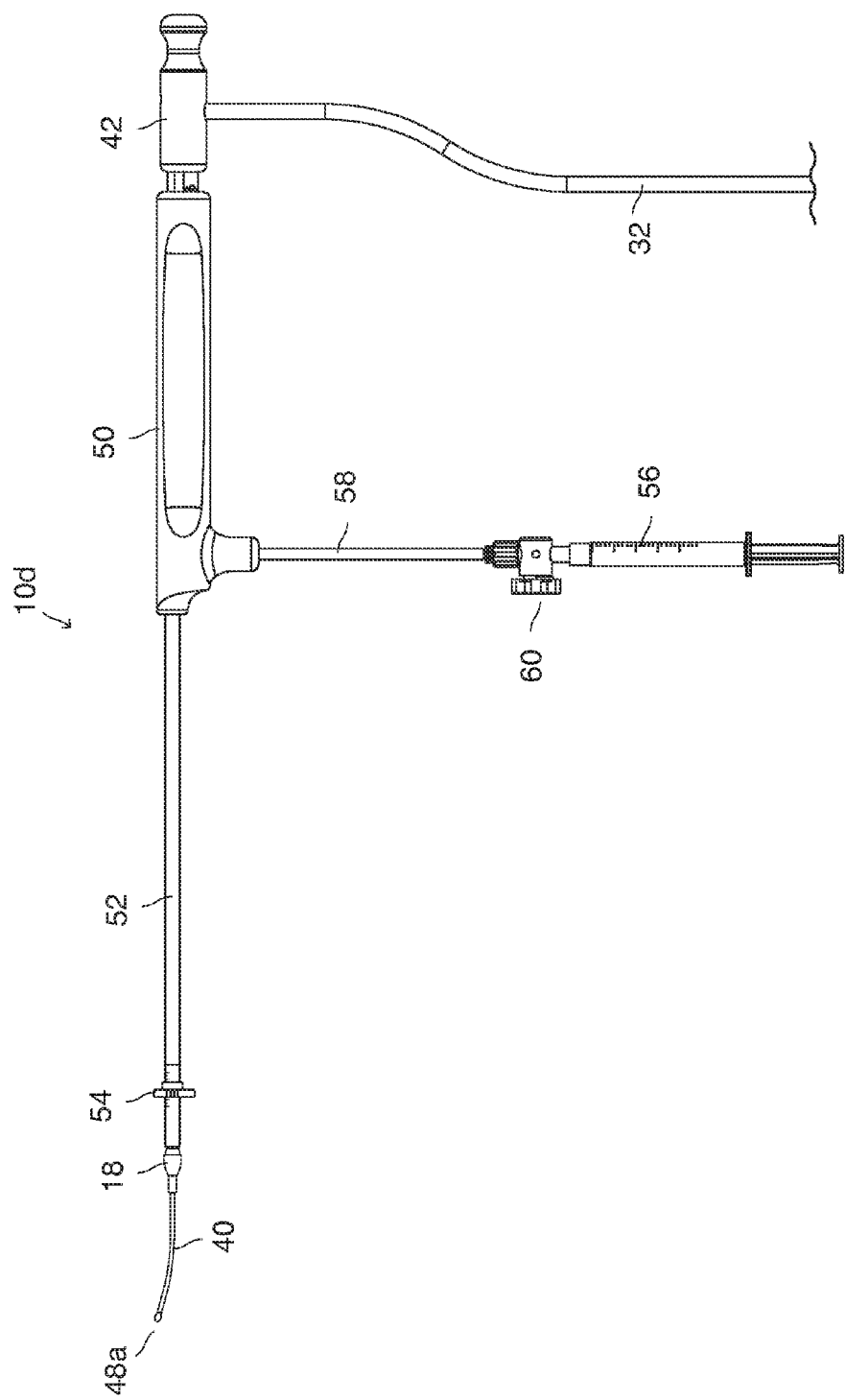
FIG. 46 is a side view of a uterine embryo retrieval device.
Figure 47:
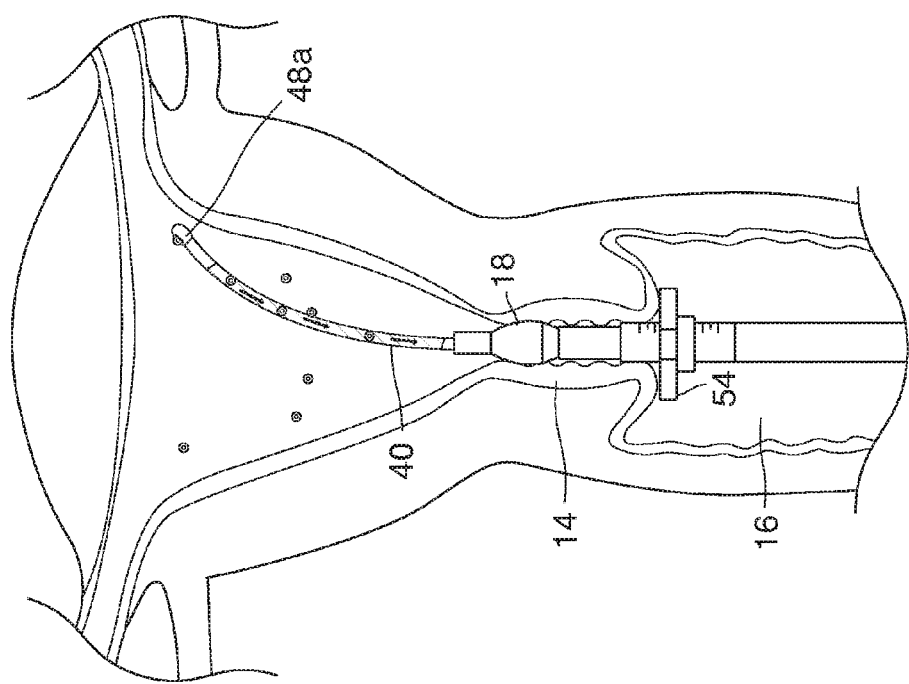
FIG. 47 illustrates another alternative lavage process using the device of FIG. 46.
Figure 48:
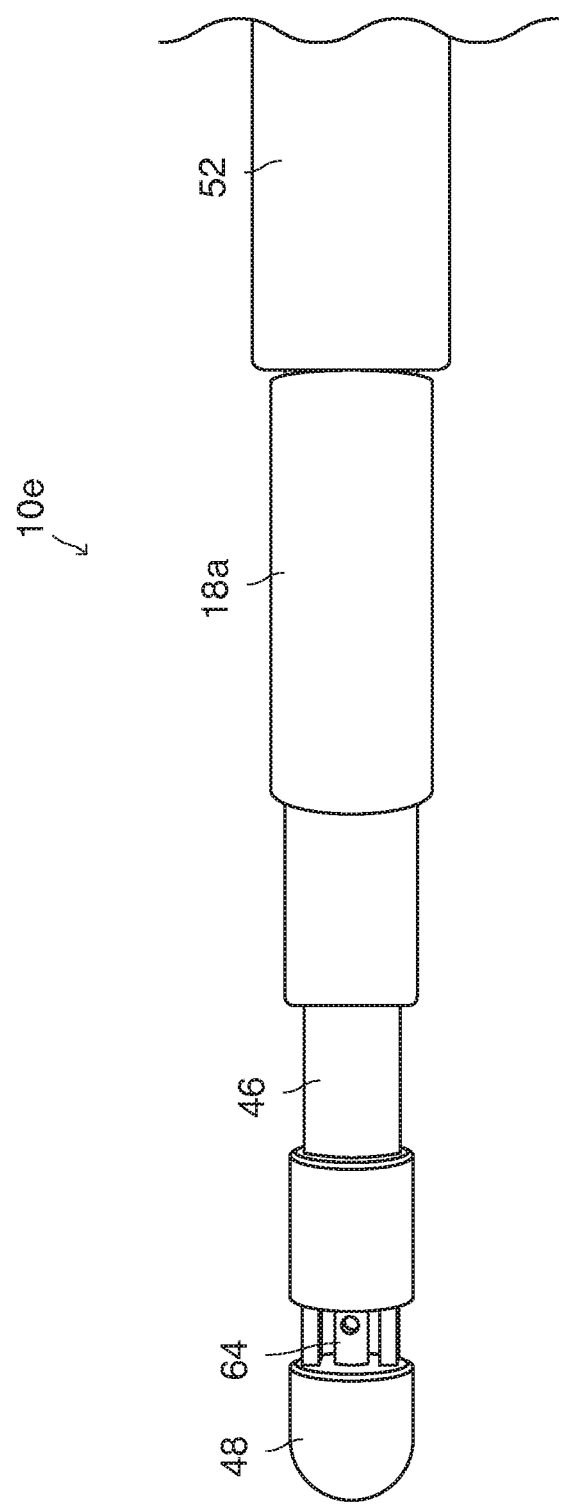
FIGS. 48 and 49 are side views of another alternative implementation of the lavage device.
Figure 49:
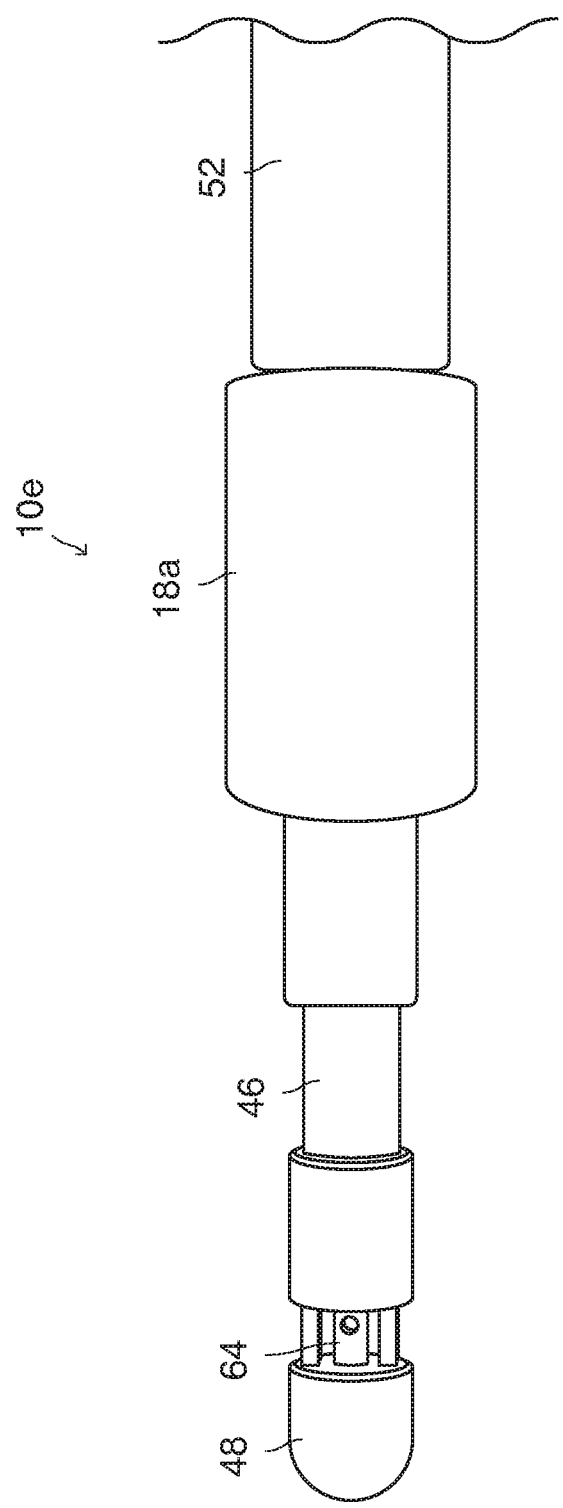
Figure 50:
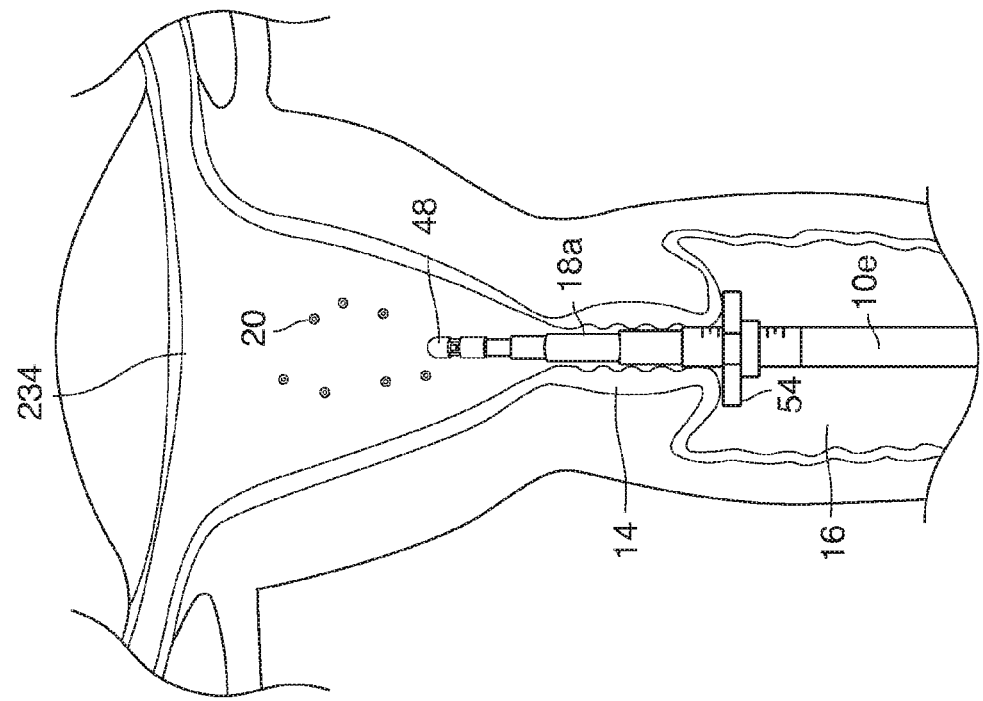
FIGS. 50 and 51 illustrate another alternative lavage process using the lavage device of FIGS. 48 and 49.

Referring to FIGS. 46 and 47, a uterine embryo retrieval device 10d having an inner catheter 40 that terminates in an atraumatic, semi-permeable absorbent head 48a includes a suction recovery line 32 but no fluid inlet line. The absorbent head 48a has a swabbing, sponge-like effect that absorbs blastocysts 20 in the uterine cavity, which are then suctioned through the inner catheter 40 and the suction recovery line 32. The device 10d is steerable so the operator can move the absorbent head 48a to different regions of the uterine cavity. Alternatively, the device 10d does not include a suction recovery line and the blastocysts 20 are recovered on the absorbent head 40a.

Figure 51:
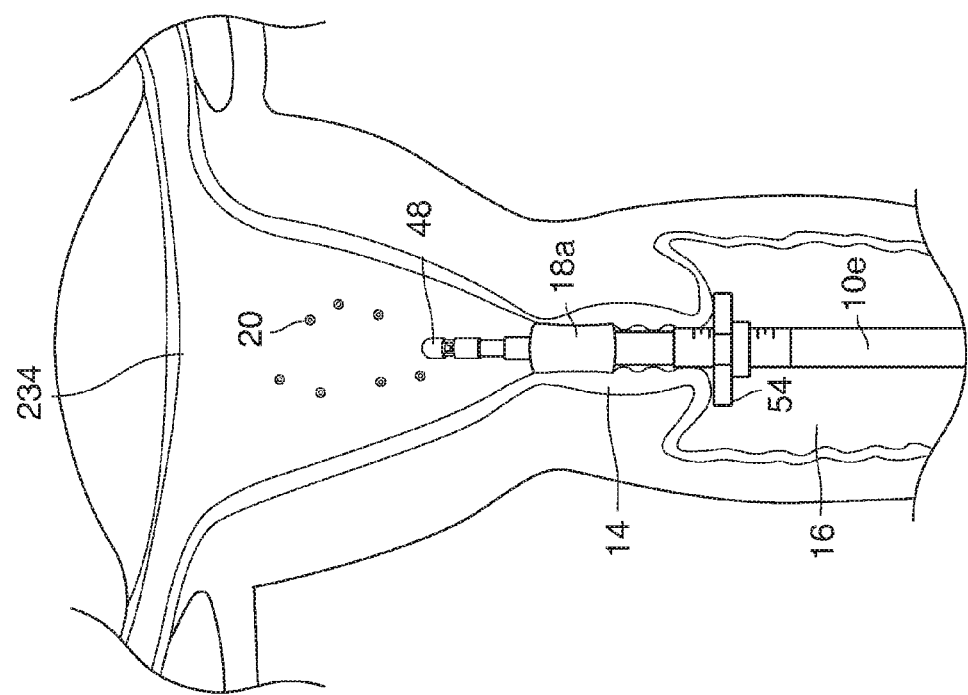

Referring to FIGS. 48-51, a lavage device 10e includes an activatable seal in the form of expandable foam 18a. The foam 18a is compressed prior to insertion and expands within the cervix to seal the uterine cavity from the external environment, as illustrated in FIG. 51.

Figure 52:
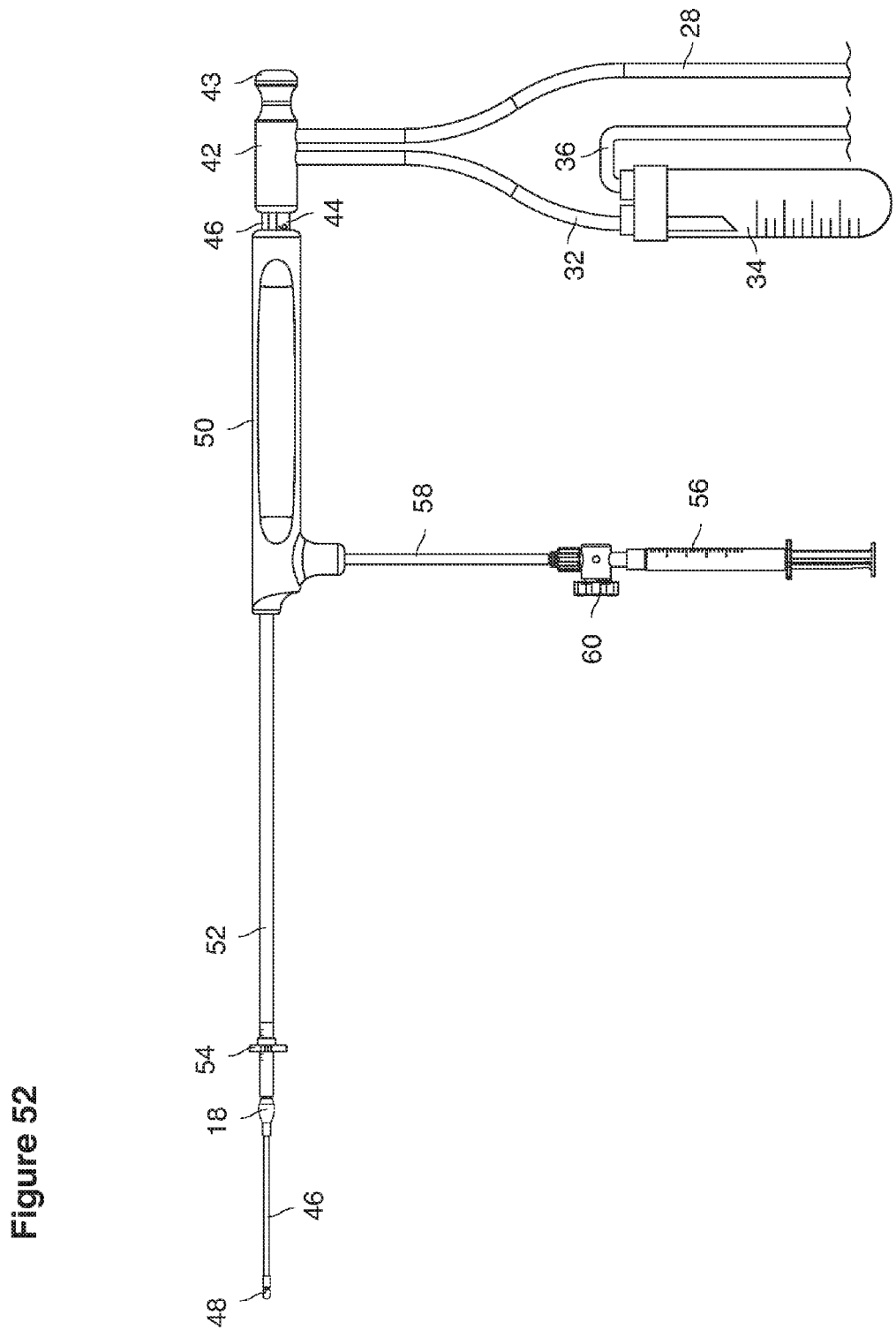
FIG. 52 is a side view of another alternative implementation of the lavage device.

Referring to FIG. 52, rather than having the collection bottle 34 mounted to the cart 100, as shown in FIG. 15, the collection bottle 34 can hang off the device 10 with the suction line 36 running to the cart 100.

A number of embodiments of the invention have been described. Nevertheless, it will be understood that various modifications may be made without departing from the spirit and scope of the invention. Accordingly, other embodiments are within the scope of the following claims.

What is claimed is:

1. A device for recovering one or more blastocysts from a uterus of a human, comprising:
    an outer guide member for insertion into a cervical canal of the human, the outer guide member including a seal for isolating the uterus from an external environment, the outer guide member defining a lumen having a longitudinal axis;
    an inner catheter located within the lumen and slidable along the longitudinal axis of the lumen relative to the outer guide member, the catheter having a distal tip positionable distally of the seal to extend into the uterus,
    the inner catheter defining a fluid delivery lumen terminating at a fluid delivery port for delivering fluid into the uterus, and the device defining a suction port for aspirating fluid and entrained blastocysts from the uterus such that in use fluid is deliverable from the fluid delivery port to travel through the suction port to the uterus; and
    a priming cap configured to cover the fluid delivery and suction ports to provide sealing to allow priming of the device prior to use.

2. The device of claim 1, wherein the inner catheter includes a tubular member that surrounds the fluid delivery lumen, an outflow lumen for aspirating fluid and entrained blastocysts being defined between the tubular member and the fluid delivery lumen.

3. The device of claim 1, wherein the inner catheter includes an atraumatic tip positioned distally of the fluid delivery port.

4. The device of claim 1, wherein the fluid delivery port is non-circular in shape to provide directional control of fluid spray.

5. The device of claim 1, wherein the seal is activatable, the seal including a balloon collar.

6. The device of claim 1, wherein the seal is activatable, the seal including an expandable foam.

7. The device of claim 1, wherein the outer guide member includes a cervical stop adjustably mounted on the outer guide member relative to the seal for positioning against an external cervical os.

8. The device of claim 7, further comprising markings for setting a distance between the seal and the cervical stop.

9. The device of claim 7, wherein the cervical stop is configured to be clamped in a position along the outer guide member.

10. The device of claim 1, wherein the fluid delivery port comprises two diametrically opposed ports.

11. The device of claim 10, wherein the two ports are non-circular in shape to provide directional control of fluid spray.

12. The device of claim 11 wherein a proximal side of at least one of the ports is perpendicular to the longitudinal axis and a distal side of the at least one of the ports diverges from the longitudinal axis at an obtuse angle.

13. The device of claim 1 further comprising an atraumatic tip, wherein the suction port includes a plurality of fluid suction ports that are defined by the atraumatic tip.

14. A device for recovering one or more blastocysts from a uterus of a human, comprising:
    an outer guide member for insertion into a cervical canal of the human, the outer guide member including a seal for isolating the uterus from an external environment, the outer guide member defining a lumen having a longitudinal axis;
    an inner catheter located within the lumen and slidable along the longitudinal axis of the lumen relative to the outer guide member, the catheter having a distal tip positionable distally of the seal to extend into the uterus,
    the inner catheter defining a fluid delivery lumen terminating at a fluid delivery port for delivering fluid into the uterus, and the device defining a suction port for aspirating fluid and entrained blastocysts from the uterus; and
    a priming cap configured to cover the fluid delivery and suction ports to provide sealing to allow priming of the device prior to use.

15. The device of claim 14, wherein the fluid delivery port is defined in a circumferential wall of the fluid delivery lumen such that the fluid is delivered radially from the fluid delivery lumen to travel through the suction port to the uterus.

* * * * *